US007262204B2

(12) United States Patent
Collins et al.

(10) Patent No.: US 7,262,204 B2
(45) Date of Patent: Aug. 28, 2007

(54) MODULATION OF CCR4 FUNCTION

(75) Inventors: Tassie Collins, San Mateo, CA (US); Daniel J. Dairaghi, Palo Alto, CA (US); Hossen Mahmud, San Antonio, TX (US); Brian E. McMaster, Mountain View, CA (US); Julio C. Medina, San Carlos, CA (US); Thomas J. Schall, Palo Alto, CA (US); Feng Xu, Palo Alto, CA (US); Xuemei Wang, San Mateo, CA (US)

(73) Assignees: Amgen Inc., Thousand Oaks, CA (US); ChemoCentryx, Inc., Mountain View, CA (US)

( * ) Notice: Subject to any disclaimer, the term of this patent is extended or adjusted under 35 U.S.C. 154(b) by 382 days.

(21) Appl. No.: 10/654,112

(22) Filed: Sep. 2, 2003

(65) Prior Publication Data

US 2004/0039035 A1 Feb. 26, 2004

Related U.S. Application Data

(62) Division of application No. 09/975,566, filed on Oct. 11, 2001, now abandoned.

(60) Provisional application No. 60/293,781, filed on May 23, 2001, provisional application No. 60/240,022, filed on Oct. 11, 2000.

(51) Int. Cl.
*A61K 31/47* (2006.01)
*A61K 31/425* (2006.01)
*A61K 31/385* (2006.01)

(52) U.S. Cl. ............... 514/311; 514/365; 514/370; 514/442

(58) Field of Classification Search ............. 514/311, 514/365, 370, 442
See application file for complete search history.

(56) References Cited

U.S. PATENT DOCUMENTS

| 2,863,874 | A | * | 12/1958 | Gregory ............... 260/306.8 |
| 3,201,409 | A | | 8/1965 | Spivack et al. |
| 3,228,888 | A | | 1/1966 | Spivack et al. |
| 3,467,666 | A | * | 9/1969 | Dexter et al. ........... 260/306.8 |
| 3,896,223 | A | | 7/1975 | Ariyan et al. |
| 4,275,210 | A | | 6/1981 | Paget, Jr. |
| 4,826,990 | A | | 5/1989 | Musser et al. |
| 5,919,776 | A | | 7/1999 | Hagmann et al. |
| 6,207,665 | B1 | | 3/2001 | Bauman et al. |
| 6,426,360 | B1 | | 7/2002 | Weier et al. |
| 6,436,967 | B1 | | 8/2002 | Talley et al. |
| 6,498,161 | B1 | | 12/2002 | Caldwell et al. |
| 6,706,767 | B2 | | 3/2004 | Saxena et al. |
| 6,784,195 | B2 | | 8/2004 | Hale et al. |
| 2002/0173524 | A1 | | 11/2002 | Collins et al. |
| 2003/0018022 | A1 | * | 1/2003 | Collins et al. ......... 514/211.15 |

FOREIGN PATENT DOCUMENTS

| EP | 0 310 370 | 4/1989 |
| EP | 1 050 307 A1 | 11/2000 |
| EP | 01 98 1850 | 3/2005 |
| WO | WO 99/04794 A1 | 2/1999 |
| WO | WO 99/38514 A1 | 8/1999 |
| WO | WO 99/38845 A1 | 8/1999 |
| WO | WO 99/42455 A1 | 8/1999 |
| WO | WO 00/41724 A1 | 7/2000 |
| WO | WO 00/42074 A1 | 7/2000 |
| WO | WO 02/30358 A2 | 4/2002 |
| WO | WO 02/34745 A1 | 5/2002 |
| WO | PCT/US02/16395 | 10/2002 |

OTHER PUBLICATIONS

Schwarz et al., Recent development in modulating Chemokine networks, Expect Opinion on Therapeutic Patents, 1999, pp. 1471-1489.*
Fernandes et al., CA 48:4513g, Apr. 25, 1954.*
Das et al., CA 49:11626c, Sep. 10, 1955.*
Mahapatra et al., CA 50:962h, Jan. 25, 1956.*
Tripathy et al., CA 80:27161, 1974.*
Nayak et al., CA 114:23843, 1991.*
Pascual, A., 1989, "Preparation of substituted 2-aminooxazole-4-cabonitriles (translated)," *Helvetica Chimica Acta* 72(3):556-569 (with English language abstract).
Mahapatra et al., 1980, "Separation of isometric ureas and oxazoles by thin-layer chromatography," *Journal of Chromatography* 193:338-339.
Baggiolini et al., 1998, "Chemokines and Leukocyte Traffic," *Nature* 392:565-568.
Baggiolini et al., 1997, "Blocking Chemokines Receptors Is a Functional Ligand for the CC Chemokine Receptor 4," *J. Biol. Chem.* 273:1764-1768.
Imai et al., 1997, "Macrophage-Derived Chemokine Is a Functional Ligand for the CC Chemokine Receptor 4," *J. Biol. Chem.* 273:1764-1768.
Imai et al., 1998, "The T-Cell-Directed CC Chemokine TARC is a Highly Specific Biological Ligand for CC Chemokine Receptor 4," *J. Biol. Chem.* 272:15036-15042.
Kita et al., 1996, "Chemokines Active on Eosinophils: Potential Roles in Allergic Inflammation," *J. Exp. Med.* 183:2421-2426.
Muller et al., 2004, "Chemokines and Chemokine Receptors: Potential Therapeutic Targets in Multiple Sclerosis," *Curr. Drug Targets Inflamm. Allergy* 3(3):279-290.

(Continued)

*Primary Examiner*—James O. Wilson
*Assistant Examiner*—Ebenezer Sackey
(74) *Attorney, Agent, or Firm*—Jones Day

(57) ABSTRACT

Compounds and compositions are provided that bind to the CCR4 chemokine receptor and which are useful for treating diseases associated with CCR4 activity, such as contact hypersensitivity.

18 Claims, 6 Drawing Sheets

OTHER PUBLICATIONS

National Institute of Health, 2005, Web page (http:www.csr.nih.gov/review/cvsirg.htm) referring to atherosclerosis and Inflammation of the Cardiovascular System [AICS] pp. 1-5.

Sun et al., 2004, "Cytokine-Induced Enhancement of Autoimmune Inflammation in the Brain and Spinal Cord: Implications for Multiple Sclerosis," *Neuropathol. Appl. Neurobiol.* 30(4):374-384.

* cited by examiner

CCR4/TARC Competition Assay
with Compound 1.1

1.1

| Best-fit values | |
|---|---|
| BOTTOM (Constant) | 200.0 |
| TOP | 1912 |
| LOGEC50 | -6.912 |
| HILLSLOPE | -0.6641 |
| EC50 | 1.2250e-007 |

CCR4/TARC Competition Assay
with Compound 1.2

1.2

| Best-fit values | |
|---|---|
| BOTTOM (Constant) | 200 |
| TOP | 1940 |
| LOGEC50 | -6.72 |
| HILLSLOPE | -0.664 |
| EC50 | 1.890e-007 |

CCR4/TARC Competition Assay with Compound 1.3

1.3

| Best-fit values | |
|---|---|
| BOTTOM | 289 |
| TOP | 1850 |
| LOGEC50 | -6.92 |
| HILLSLOPE | -0.933 |
| EC50 | 1.200e-007 |

CEM Migration Assays with CCR4/TARC and Compound 1.2

Effect of Compound 1.3 on CEM Calcium Response

Effect of Compound 1.2 on CEM Calcium Response

MODULATION OF CCR4 FUNCTION

CROSS-REFERENCES TO RELATED APPLICATIONS

This application is a Divisional of application Ser. No. 09/975,566, filed Oct. 11, 2001, now abandoned which claims the benefit of Provisional Application Ser. No. 60/240,022, filed Oct. 11, 2000, and further claims the benefit of Provisional Application Ser. No. 60/293,781, filed May 23, 2001, the disclosures of each being incorporated herein by reference.

STATEMENT AS TO RIGHTS TO INVENTIONS MADE UNDER FEDERALLY SPONSORED RESEARCH AND DEVELOPMENT

Not applicable

Subject matter disclosed herein was made as a result of activities undertaken within the scope of a joint research agreement between ChemoCentryx, Inc. and Tularik Inc.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165-183 (1991), Schall, et al., *Curr. Opin. Immunol.* 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are four classes of chemokines, CXC ($\alpha$), CC ($\beta$), C($\gamma$), and $CX_3C$ ($\delta$), depending on whether the first two cysteines are separated by a single amino acid (C—X—C), are adjacent (C—C), have a missing cysteine pair (C), or are separated by three amino acids ($CX_3C$). The a-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381:661-666 (1996)). The C chemokine lymphotactin shows specificity for lymphocytes (Kelner, et al., *Science*, 266: 1395-1399 (1994)) while the $CX_3C$ chemokine fractalkine shows specificity for lymphocytes and monocytes (Bazan, et al., *Nature*, 385:640-644 (1997).

Chemokines bind to specific cell-surface receptors belonging to the family of G-protein-coupled seven-transmembrane-domain proteins (reviewed in Horuk, *Trends Pharm. Sci.* 15:159-165 (1994)) which are termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to $\beta$-chemokines with the following characteristic pattern: CCR1 (or "CKR-1" or "CC-CKR-1") to MIP-1$\alpha$, MIP-1$\beta$, MCP-3, RANTES (Ben-Barruch, et al., *J. Biol. Chem.*, 270:22123-22128 (1995); Neote, et al., *Cell*, 72:415425 (1993)); CCR2A and CCR2B (or "CKR-2A"/"CKR-2A" or "CC-CKR-2A"/"CC-CKR2A") to MCP-1, MCP-3, MCP-4; CCR3 (or "CKR-3" or "CC-CKR-3") to eotaxin, RANTES, MCP; (Ponath, et al., *J. Exp. Med.*, 183:2437-2448 (1996)); CCR4 (also referred to as "CKR4", "CC-CKR4" or "CMKBR4"), to TARC, MDC (Imai et al. (1998) *J. Biol. Chem.* 273:1764-1768); CCR5 (or "CKR-5" or "CC-CKR-5") to MIP-1$\alpha$, RANTES, MIP-1$\beta$ (Sanson, et al., *Biochemistry*, 35:3362-3367 (1996)); CCR6 to MIP-3 alpha (Greaves, et al., *J. Exp. Med.*, 186:837-844 (1997)); CCR7 to MIP-3 beta and 6Ckine (Campbell, et al., *J. Cell. Biol.*, 141:1053-1059(1998)); CCR8 to I-309, HHV8 vMIP-I, HFV-8 vMIP-II, MCV vMCC-I (Dairaghi, et al., *J. Biol. Chem.*, 274:21569-21574 (1999)); CCR9 to TECK (Zaballos, et al., *J. Immunol.*, 162:5671-5675 (1999)), D6 MIP-1 beta, RANTES, and MCP-3 (Nibbs, et al., *J. Biol. Chem.*, 272:32078-32083 (1997)), the Duffy blood-group antigen to IL-8, Gro$\alpha$, RANTES, MCP-1 (Chaudhun et al. (1994) *J. Biol. Chem.* 269:7835-7838, Murphy et al. (2000) *Pharm. Rev.* 52:145-176) and CCR10 to CTACK, CCL28 (Jarmin et al. (2000) *J. Immunol.* 164:3460-3464, Homey et al. (2000) *J. Immunol.* 164:3465-3470, Wang et al. (2000) *J. Biol. Chem.* 275:22313-22323).

Chemokine receptors, such as CCR1, CCR2, CCR2A, CCR2B, CCR3, CCR4, CCR5, CCR6, CCR7, CCR8, CCR9, CXCR1, CXCR2, CXCR3, CXCR4, CXCR5, $CX_3CR1$ and XCR1 have been implicated as being important mediators of inflammatory and immunoregulatory disorders and diseases, including asthma and allergic diseases, as well as autoimmune pathologies such as rheumatoid arthritis and atherosclerosis.

The CCR4 chemokine receptor, first identified by Power et al. (Power et al. (1995) *J. Biol. Chem.* 270:19495-19500), is expressed primarily in peripheral blood T lymphocytes. CCR4 is involved in T lymphocyte homing to the skin and lungs (see, e.g., Campbell et al. (1999) *Nature* 400:776-780, Gonzalo et al. (1999) *J. Immunol.* 163:403-411, Lloyd et al. (2000) *J. Exp. Med.* 191:265-273, Kawasaki et al. (2001) *J. Immunol.* 166:2055-2062).

The identification of compounds that modulate the function of CCR4 represents an attractive approach to the development of therapeutic agents for the treatment of inflammatory conditions and diseases associated with CCR4 activation, such as psoriasis, asthma and allergic diseases.

SUMMARY OF THE INVENTION

The present invention is directed to compounds which are modulators of CCR4 chemokine receptor function and are useful in the prevention or treatment of inflammatory conditions and diseases such as allergic diseases, psoriasis, atopic dermatitis and asthma. The invention is also directed to pharmaceutical compositions comprising these compounds and the use of these compounds and compositions in the prevention or treatment of diseases in which CCR4 chemokine receptors are involved.

In one aspect, the present invention provides compounds having the general formula (I):

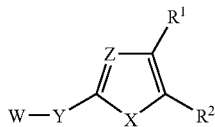

wherein W is selected from aryl, heteroaryl, $(C_1-C_8)$alkyl, heteroalkyl, cycloalkyl and heterocycloalkyl; X is selected from $N(R^5)$, S, O, $C(R^3)=C(R^4)$, $N=C(R^4)$, and optionally, when Z is N, X can be $C(R^6)(R^7)$; Y is selected from a bond, $N(R^5)$, $N(R^5)-(C_1-C_8)$alkylene, O, S and $S(O)_n$, wherein the integer n is 1 or 2; and Z is selected from N and $C(R^8)$. $R^1$ and $R^2$ are independently selected from H, halogen, CN, $CO_2R'$, $CONR'R''$, $(C_1-C_8)$alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from N, O and S, wherein $R'$ and $R''$ are independently selected from H, $(C_1-C_8)$alkyl and aryl. When $R'$ and $R''$ are attached to nitrogen, they may be combined with the nitrogen atom to form a 5-, 6-, or 7-membered ring. $R^3$, $R^4$ and $R^8$ are independently selected from H, halogen, CN, OH, $(C_1-C_8)$alkyl, heteroalkyl, aryl, heteroaryl, $O(C_1-C_8)$alkyl, $N(R^6)(R^7)$ and $OR^9$; $R^5$ is selected from H, $(C_1-C_8)$alkyl, heteroalkyl, aryl and heteroaryl; $R^6$ and $R^7$ are independently selected from H, $(C_1-C_8)$alkyl, heteroalkyl, aryl and heteroaryl; and $R^9$ is selected from $(C_1-C_8)$alkyl, heteroalkyl and haloalkyl; with the provisos that $R^1$ is other than phenyl, when W is phenyl or unsubstituted naphthyl, X is S, Y is NH, and Z is N; and $R^2$ is other than H when W is unsubstituted phenyl, X is S, Y is NH, Z is N and $R^1$ is $(C_1-C_8)$alkyl.

Unless otherwise indicated, the compounds provided in the above formula are meant to include pharmaceutically acceptable salts and prodrugs thereof A number of embodiments are preferred within the above formula. Among the preferred, but separate, embodiments, are those wherein Z is N; wherein X is S; wherein Y is $N(R^5)$; wherein Z is N, X is S and Y is $N(R^5)$; wherein W is aryl or heteroaryl; wherein W is aryl or heteroaryl and aryl is phenyl or naphthyl; wherein W is aryl or heteroaryl and heteroaryl is pyridyl or quinolyl; wherein $R^1$ and $R^2$ are independently H or $(C_1-C_8)$alkyl; wherein $R^1$ and $R^2$ combine to form a fused 6-membered aryl or heteroaryl ring; wherein W is aryl or heteroaryl, X is S, Y is $N(R^5)$, Z is N, and $R^1$ and $R^2$ are independently H or $(C_1-C_8)$alkyl; wherein W is aryl or heteroaryl, X is S, Y is $N(^5)$, Z is N, and $R^1$ and $R^2$ combine to form a fused 6-membered aryl or heteroaryl ring.

In one group of preferred embodiments, the compound is represented by formula (Ia):

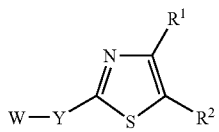

wherein W, Y, $R^1$ and $R^2$ have the meanings provided above.

In another aspect, the present invention provides a composition comprising a pharmaceutically acceptable carrier and a compound of formula I as provided above, or a compound of formula I wherein $R^1$ is phenyl, when W is phenyl or unsubstituted naphthyl, X is S, Y is NH, and Z is N; and $R^2$ is H when W is unsubstituted phenyl, X is S, Y is NH, Z is N and $R^1$ is $(C_1-C_8)$alkyl.

In still another aspect, the present invention provides a method of treating a CCR4-mediated condition or disease, comprising administering to a subject in need of such treatment, a therapeutically effective amount of a composition as described herein.

In preferred, but separate, embodiments of this aspect of the invention the CCR4-mediated condition or disease is selected from an allergic disease, psoriasis, atopic dermatitis and asthma; the CCR4-mediated condition or disease is an allergic disease; the CCR4-mediated condition or disease is an allergic disease and the allergic disease is selected from systemic anaphylaxis, hypersensitivity responses, drug allergies, insect sting allergies and food allergies; the CCR4-mediated condition or disease is psoriasis; the CCR4-mediated condition or disease is atopic dermatitis; the CCR4-mediated condition or disease is asthma; the CCR4-mediated condition or disease is an allergic condition and the compound is used alone or in combination with at least one therapeutic agent wherein the therapeutic agent is an antihistamine; the CCR4-mediated condition or disease is psoriasis and the compound is used alone or in combination with at least one therapeutic agent selected from a corticosteroid, a lubricant, a keratolytic agent, a vitamin $D_3$ derivative, PUVA and anthralin; the CCR4-mediated condition or disease is atopic dermatitis and the compound is used alone or in combination with at least one therapeutic agent selected from a lubricant and a corticosteroid; the CCR4-mediated condition or disease is asthma and the compound is used alone or in combination with at least one therapeutic agent selected from a β2-agonist and a corticosteroid; the compound interferes with the interaction between CCR4 and a ligand; the subject is a human.

In yet another aspect, the present invention provides a a method of modulating CCR4 function in a cell, comprising contacting the cell with a therapeutically effective amount of a compound of formula I.

In still another aspect, the present invention provides a method for modulating CCR4 function, comprising contacting a CCR4 protein with a therapeutically effective amount of a compound of formula I.

In another aspect, the present invention provides compositions and methods using compounds having the general formula:

$$Ar^1-X-Ar^2 \quad (II)$$

in which the symbols $Ar^1$ and $Ar^2$ each independently represent a substituted or unsubstituted aryl, substituted or unsubstituted heteroaryl, or a substituted or unsubstituted fused aryl-heterocyclic ring system. The letter X represents a linking group selected from —N(R)—, —C(O)S—, —CH=CHSO_2— and —SO_2N(R)— wherein R is H or a substituted or unsubstituted $(C_1-C_8)$alkyl group. In this formula, the linking group can be in either orientation relative to the $Ar^1$ and $Ar^2$ moieties. For example, the above general formula is meant to include both $Ar^1$—$SO_2$—NH—$Ar^2$ and $Ar^1$—NH—$SO_2$—$Ar^2$. These compounds are useful in compositions and methods for the treatment of CCR4-mediated conditions or diseases, particularly those recited above with reference to compounds of formula I.

DESCRIPTION OF THE INVENTION

Abbreviations and Definitions

Figure 1:
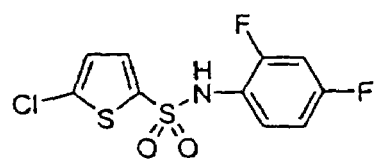
FIG. 1 is a graph showing the results of a CCR4/TARC competition assay using compound 1.1.
Figure 1:
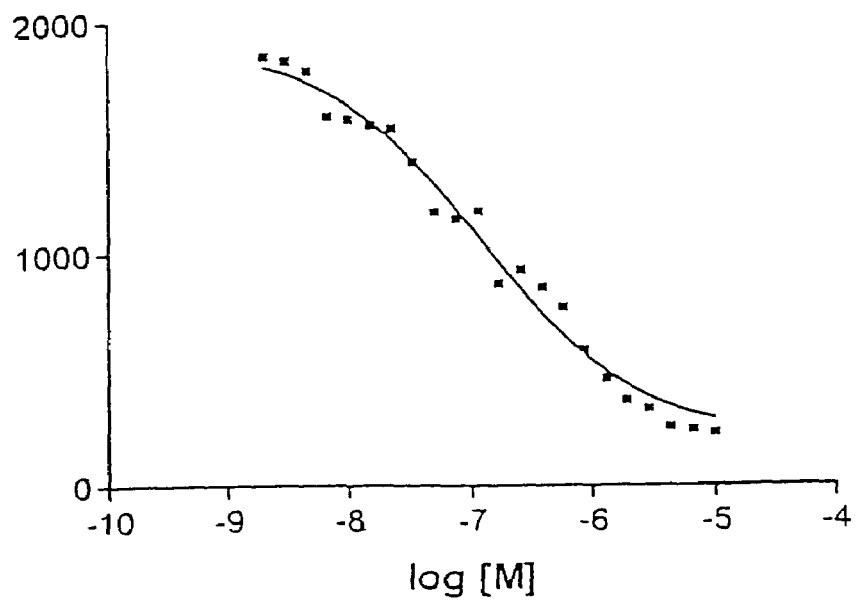
Figure 2:
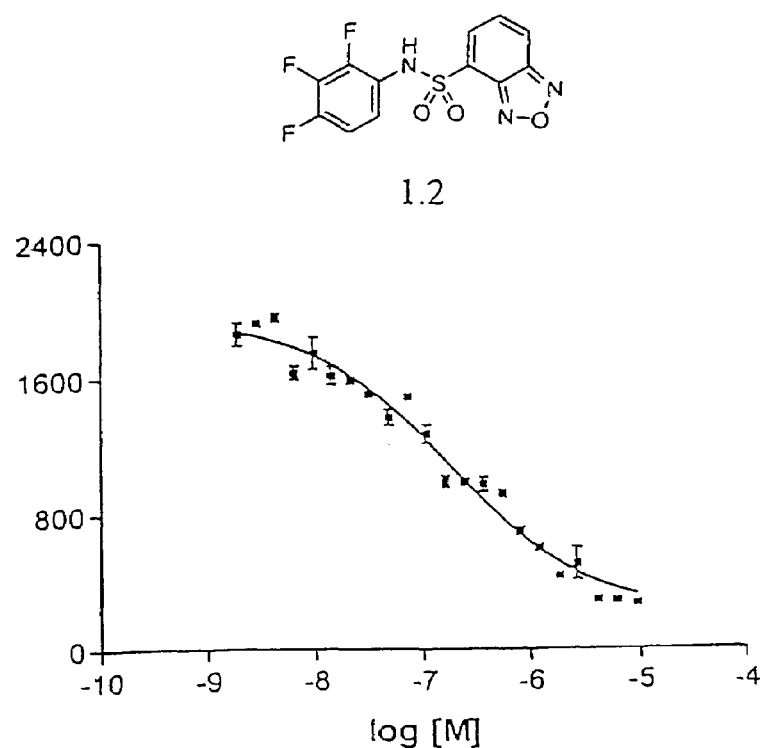
FIG. 2 is a graph showing the results of a CCR4/TARC competition assay using compound 1.2.
Figure 2:
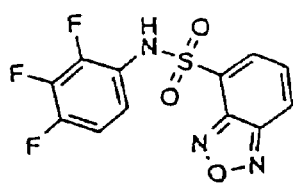
Figure 3:
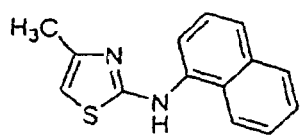
FIG. 3 is a graph showing the results of a CCR4/TARC competition assay using compound 1.3.
Figure 3:
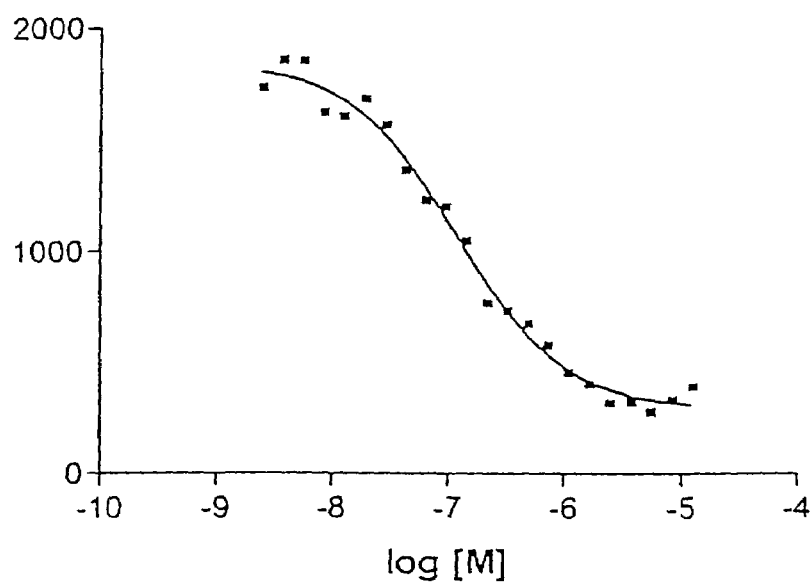
Figure 4:
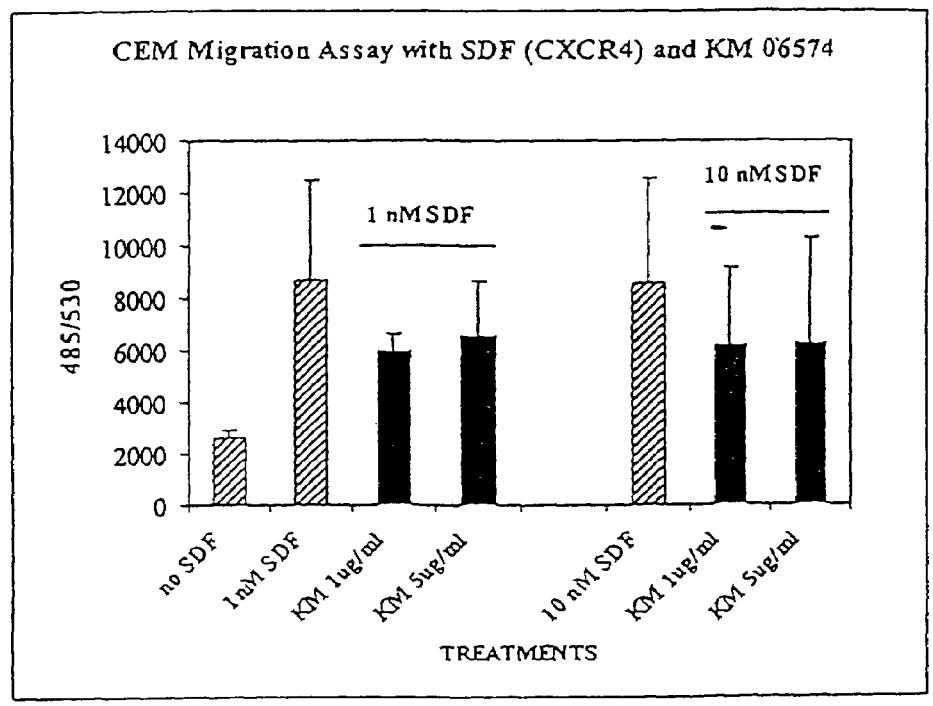
FIG. 4 illustrates the results achieved with compound 1.2 in CEM migration assays with CCR4 and TARC.
Figure 4:
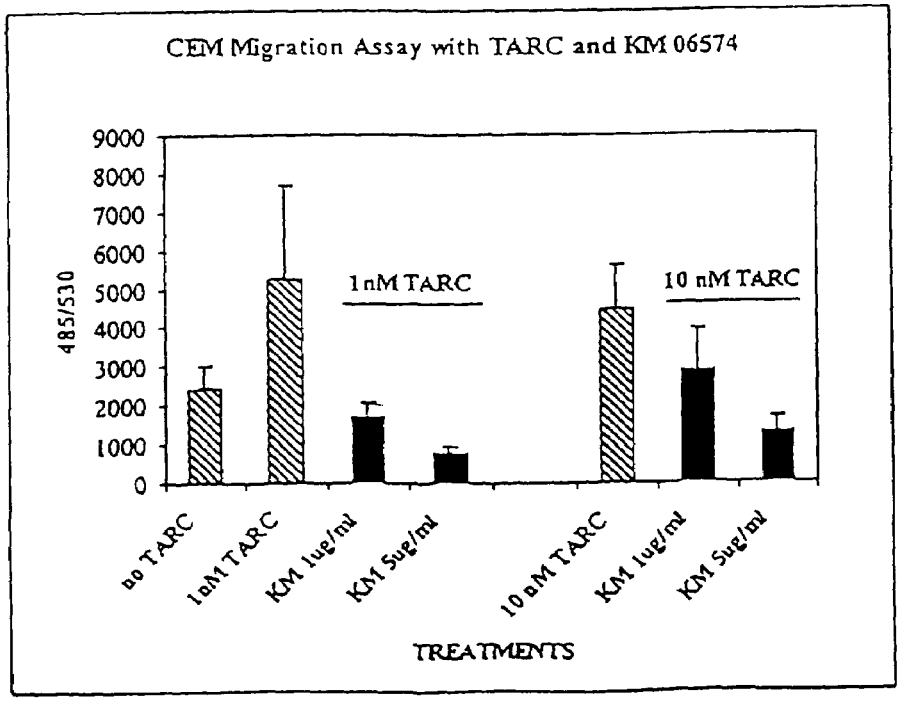
Figure 5:
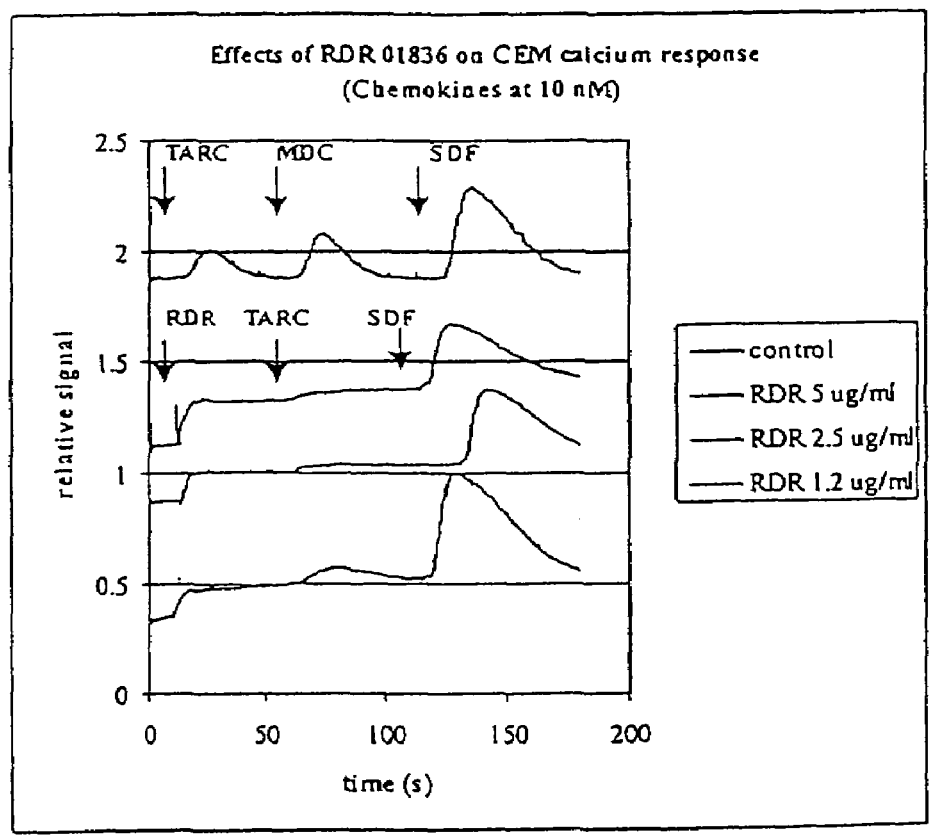
FIG. 5 illustrates the effect of compound 1.3 on CEM calcium response.
Figure 5:
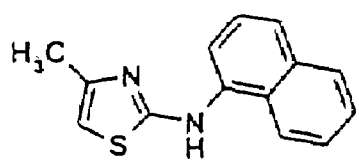
Figure 6:
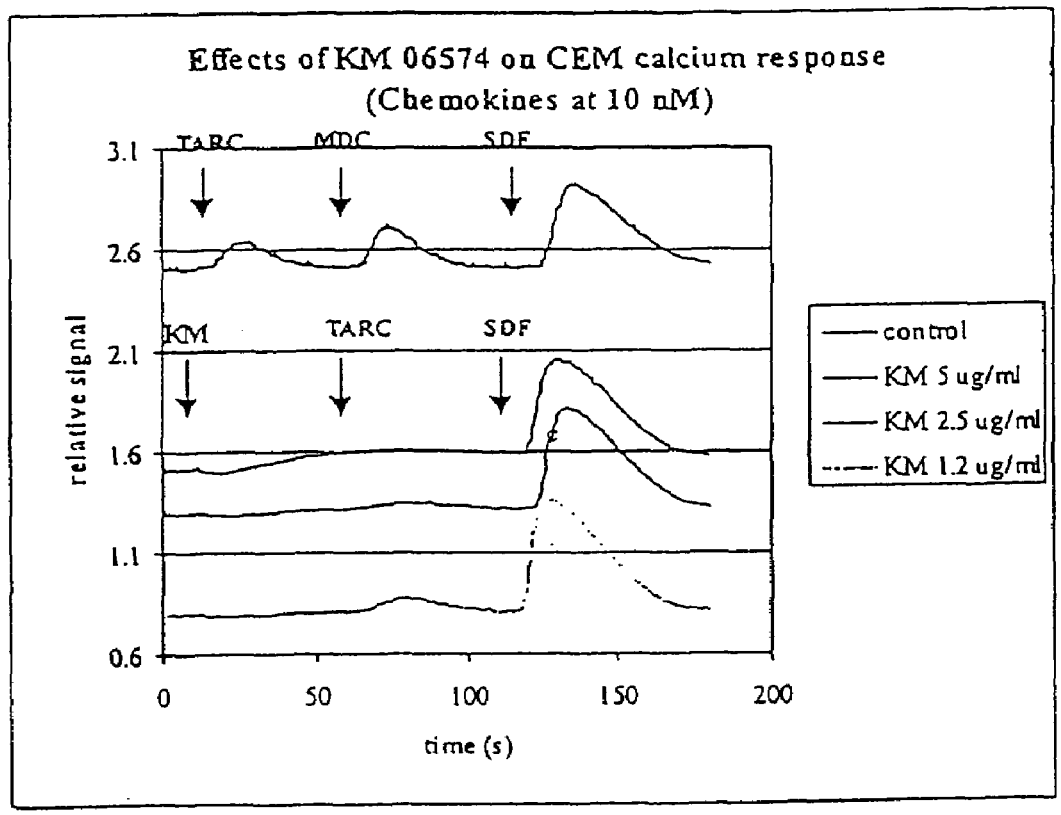
FIG. 6 illustrates the effect of compound 1.2 on CEM calcium response.
Figure 6:
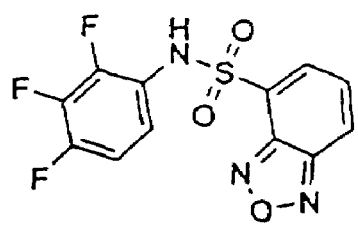

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$_{CH2}$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkyle groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R" R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R''' each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g. —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

Chemokine receptors are attractive targets for the development of antiinflammatory agents. Small molecule antagonists of chemokine receptors, e.g., CC chemokine receptors, however, are not widely known. U.S. Pat. No. 6,207,665 to Hesselgesser et al. describes piperazine derivatives as CCR1 antagonists and is hereby incorporated by reference.

The present invention is directed to compounds, compositions and methods useful in the modulation of chemokine receptor function, particularly CCR4 function. Accordingly, the compounds of the present invention are compounds which inhibit at least one function or characteristic of a mammalian CCR4 protein, for example, a human CCR4 protein.

The full-length human CCR4 protein (GenBank Accession No. X85740; SWISS-PROT Accession No. P5 1679) has been described, see, e.g, Imai et al. (1998) *J. Biol. Chem.* 273:1764-1768, and has the sequence shown in SEQ ID NO:1.

The ability of a compound to inhibit the function of CCR4, can be demonstrated in a binding assay (e.g., ligand binding or agonist binding), a signalling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

In view of the above, the present invention is directed to compounds, compositions and methods useful in the modulation of chemokine receptor activity, particularly CCR4. Accordingly, the compounds of the present invention are those which inhibit at least one function or characteristic of a mammalian CCR4 protein, for example, a human CCR4 protein. The ability of a compound to inhibit such a function can be demonstrated in a binding assay (e.g., ligand binding or promotor binding), a signalling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes).

Compounds that Modulate CCR4 Activity

CCR4 Antagonists

The present invention provides compounds having anti-inflammatory or anti-immunoregulatory activity. The compounds of the invention are thought to interfere with inappropriate T-cell trafficking by specifically modulating or inhibiting a chemokine receptor function. Chemokine receptors are integral membrane proteins which interact with an extracellular ligand, or chemokine, and mediate a cellular response to the chemokine, e.g., chemotaxis, increased intracellular calcium ion concentration. Therefore, inhibition of a chemokine receptor function, e.g., interference with a chemokine receptor-ligand interaction, will inhibit a chemokine receptor-mediated response and treat or prevent a chemokine receptor-mediated condition or disease.

Without intending to be bound by theory, it is believed that the compounds provided herein interfere with the interaction between a chemokine receptor and one or more cognate ligands. In particular, it is believed that the compounds interfere with the interaction between CCR4 and a CCR4 ligand, e.g., TARC, MDC, etc. Compounds contemplated by the invention include, but are not limited to, the exemplary compounds provided herein.

The compounds provided herein have the general formula (I):

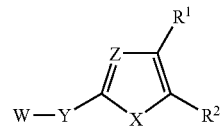

wherein W is selected from aryl, heteroaryl, ($C_1$-$C_8$)alkyl, heteroalkyl, cycloalkyl and heterocycloalkyl; X is selected from $N(R^5)$, S, O, $C(R^3)=C(R^4)$, $N=C(^4)$, and optionally, when Z is N, X can be $C(R^6)(R^7)$; Y is selected from a bond, $N(R^5)$, $N(R^5)$-($C_1$-$C_8$)alkylene, O, S and $S(O)_n$, wherein the integer n is 1 or 2; and Z is selected from N and $C(R^8)$. $R^1$ and $R^2$ are independently selected from H, halogen, CN, $CO_2R^1$, CONR'R'', ($C_1$-$C_8$)alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from N, O and S, wherein R' and R'' are independently selected from H, ($C_1$-$C_8$)alkyl and aryl. When R' and R'' are attached to nitrogen, they may be combined with the nitrogen atom to form a 5-, 6-, or 7-membered ring. $R^3$, $R^4$ and $R^8$ are independently selected from H, halogen, CN, OH, ($C_1$-$C_8$)alkyl, heteroalkyl, aryl, heteroaryl, O($C_1$-$C_8$)alkyl, $N(R^6)(R^7)$ and $OR^9$; $R^5$ is selected from H, ($C_1$-$C_8$)alkyl, heteroalkyl, aryl and heteroaryl; $R^6$ and $R^7$ are independently selected from H, ($C_1$-$C_8$)alkyl, heteroalkyl, aryl and heteroaryl; and $R^9$ is selected from ($C_1$-$C_8$)alkyl, heteroalkyl and haloalkyl; with the provisos that $R^1$ is other than phenyl, when W is phenyl or unsubstituted naphthyl, X is S, Y is NH, and Z is N; and $R^2$ is other than H when W is unsubstituted phenyl, X is S, Y is NH, Z is N and $R^1$ is ($C_1$-$C_8$)alkyl.

Embodiments represented by formula I can be appreciated by replacing the ring system containing X and Z with an appropriate scaffold, wherein the attachment points represent the attachment of Y, $R^1$ and $R^2$ groups:

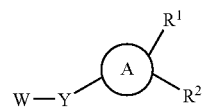

For example, the ring system or "scaffold" is meant to include the following (including substituted versions thereof) wherein the "A" ring is selected from the following embodiments:

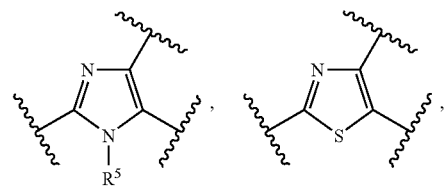

-continued

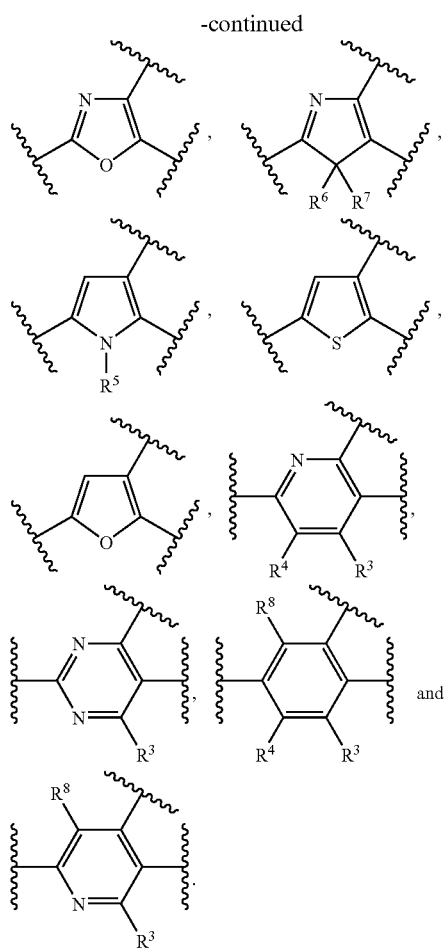

In one group of preferred embodiments Z is N. In another group, X is S. In still another group of preferred embodiments, Y is $N(R^5)$. Particularly preferred are those embodiments that combine each of these preferred groups. Accordingly, in one group of particularly preferred embodiments X is S, Y is $N(R^5)$ and Z is N.

In another group of preferred embodiments, W is selected from aryl and heteroaryl. Particularly preferred are those embodiments in which aryl is phenyl or naphthyl. Other particularly preferred embodiments are those in which heteroaryl is pyridyl or quinolyl. In separate, but preferred embodiments, $R^1$ and $R^2$ are independently H or $(C_1-C_8)$ alkyl. In still other separate, but preferred embodiments, $R^1$ and $R^2$ combine to form a fused 6-membered aryl or heteroaryl ring. In each of the above groups of preferred embodiments, $R^5$ is most preferably H.

In another group of preferred embodiments, the compounds of the invention have the formula(I), wherein W is selected from substituted naphthyl, pyridyl quinolyl, $(C_1-C_8)$alkyl, heteroalkyl, cycloalkyl and heterocycloalkyl; X is selected from $N(R^5)$, S, O, $C(R^3)=C(^4)$, $N=C(R^4)$, and optionally, when Z is N, X can be $C(R^6)(R^7)$; Y is selected from a bond, $N(R^5)$, $N(R^5)$-$(C_1-C_8)$alkylene, O, S and $S(O)_n$, wherein the integer n is 1 or 2; and Z is selected from N and $C(R^8)$. $R^1$ and $R^2$ are independently selected from H, halogen, CN, $CO_2R'$, $CONR'R''$, $(C_1-C_8)$alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from N, O and S, wherein R' and R" are independently selected from H, $(C_1-C_8)$alkyl and aryl. When R' and R" are attached to nitrogen, they may be combined with the nitrogen atom to form a 5-, 6-, or 7-membered ring. $R^3$, $R^4$ and $R^8$ are independently selected from H, halogen, CN, OH, $(C_1-C_8)$alkyl, heteroalkyl, aryl, heteroaryl, $O(C_1-C_8)$alkyl, $N(R^6)(R^7)$ and $OR^9$; $R^5$ is selected from H, $(C_1-C_8)$alkyl, heteroalkyl, aryl and heteroaryl; $R^6$ and $R^7$ are independently selected from H, $(C_1-C_8)$alkyl, heteroalkyl, aryl and heteroaryl; and $R^9$ is selected from $(C_1-C_8)$alkyl, heteroalkyl and haloalkyl.

A number of embodiments are particularly preferred within this group and are separately provided as those wherein Z is N; wherein X is S; wherein Y is $N(R^5)$; wherein Z is N, X is S and Y is $N(R^5)$; wherein W is substituted naphthyl; wherein W is pyridyl or quinolyl; wherein $R^1$ is other than phenyl; wherein $R^1$ and $R^2$ are independently H or $(C_1-C_8)$alkyl; wherein $R^1$ and $R^2$ combine to form a fused 6-membered aryl or heteroaryl ring; wherein W is substituted naphthyl, X is S, Y is $N(R^5)$, Z is N, and $R^1$ and $R^2$ are independently H or $(C_1-C_8)$alkyl; wherein W is substituted naphthyl, X is S, Y is $N(R^5)$, Z is N, and $R^1$ and $R^2$ combine to form a fused 6-membered aryl or heteroaryl ring; wherein W is pyridyl or quinolyl, X is S, Y is $N(R^5)$, Z is N, and $R^1$ and $R^2$ are independently H or $(C_1-C_8)$alkyl; and wherein W is pyridyl or quinolyl, X is S, Y is $N(R^5)$, Z is N, and $R^1$ and $R^2$ combine to form a fused 6-membered aryl or heteroaryl ring.

In a particularly preferred group of embodiments, the A ring is a thiazole ring (see formula Ia).

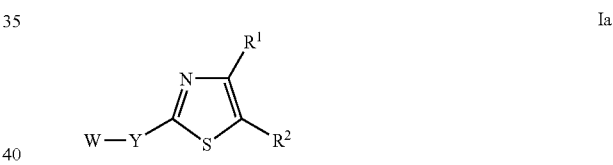

Ia

In formula Ia, W, Y, $R^1$ and $R^2$ have the meanings (and preferred groupings) provided above. Exemplary structures within this preferred group of embodiments are shown below.

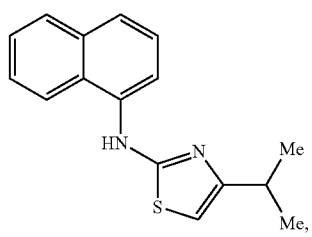

12

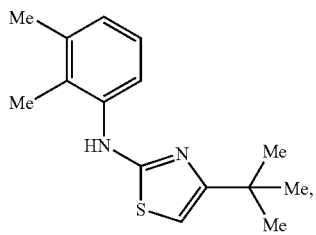

2

-continued
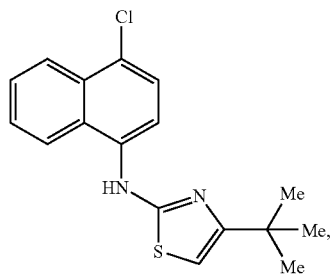
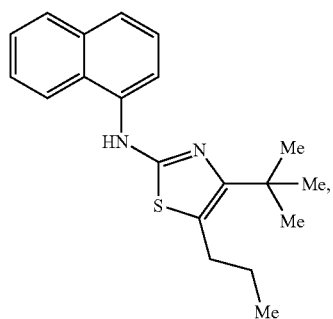
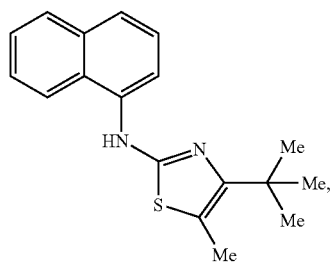
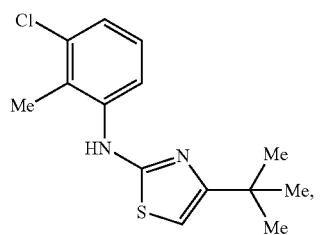
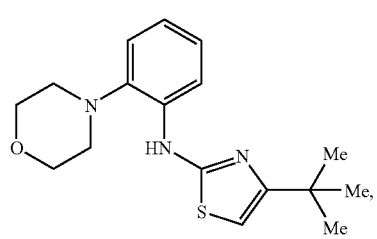
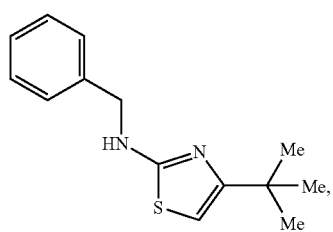
-continued
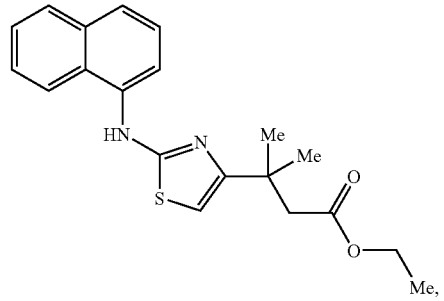
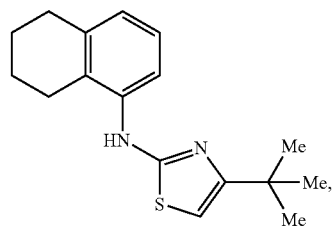
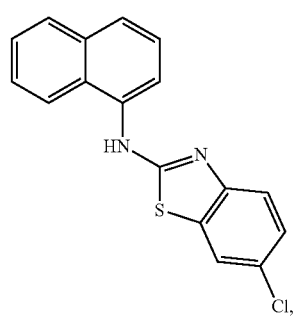
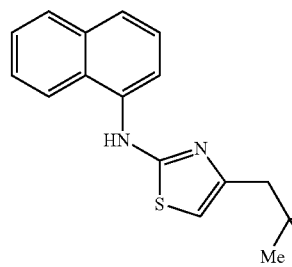
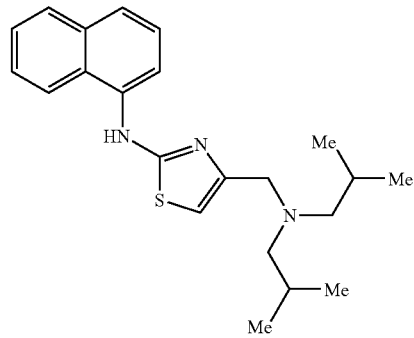

-continued

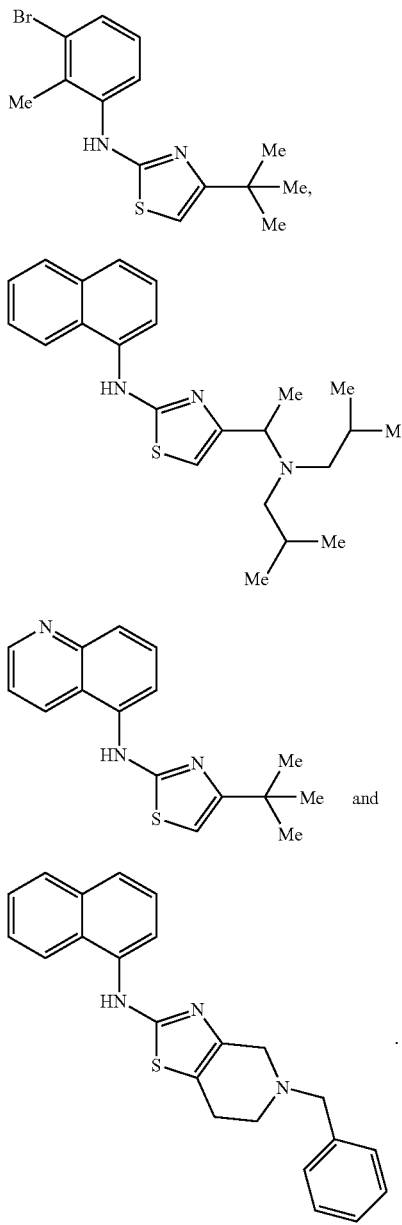

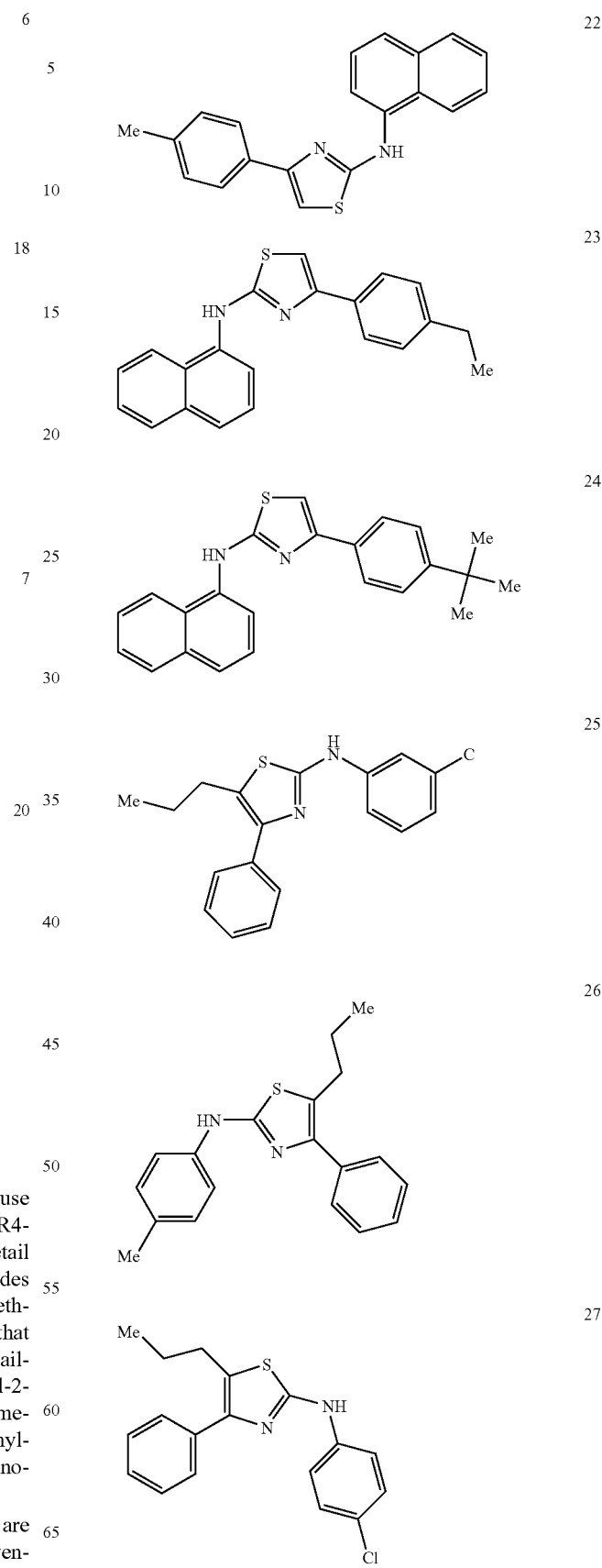

The compounds provided above are contemplated for use in compositions and methods for the treatment of CCR4-mediated conditions and diseases as described in more detail below. However, the present invention further includes aspects directed to pharmaceutical compositions and methods using compounds that are known, particularly those that are commercially available. Exemplary commercially available compounds include: 4(1,1-dimethylethyl)-N-phenyl-2-thiazolamine, 4-methyl-N-phenyl-2-thiazolamine, 4-(1-methylethyl)-N-phenyl-2-thiazolamine, 4-dodecyl-N-phenyl-2-thiazolamine, 2-anilino-4-isobutyl-thiazole, and 2-anilino-4-methyl-thiazole picrate.

Still other commercially available compounds that are useful in the composition and method aspects of this invention include:

-continued

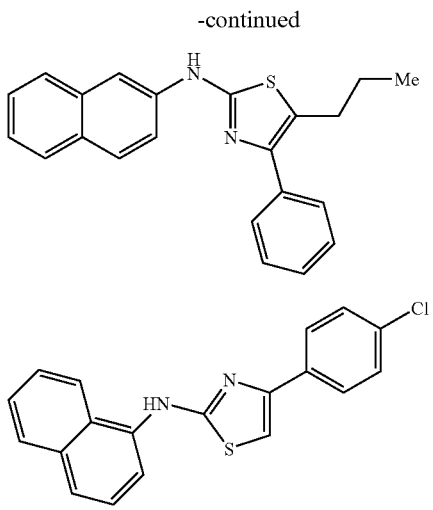

Synthesis of CCR4 Antagonists

Synthesis routes to the compounds provided above are described in the Examples. One of skill in the art will appreciate that the substituents (e.g., R', R", R''', etc.) can be altered before, during or after preparation of the heterocyclic scaffolding and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group.

Compositions that Modulate CCR4 Activity

In another aspect, the present invention provides compositions that modulate CCR4 activity.

Generally, the compositions will comprise a pharmaceutically acceptable excipient and a compound having the formula provided above as formula I:

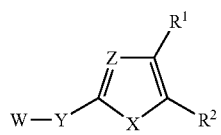

wherein W is selected from aryl, heteroaryl, $(C_1-C_8)$alkyl, heteroalkyl, cycloalkyl and heterocycloalkyl; X is selected from $N(R^5)$, S, O, $C(R^3)=C(R^4)$, $N=C(R^4)$, and optionally, when Z is N, X can be $C(R^6)(R^7)$; Y is selected from a bond, $N(R^5)$, $N(R^5)-(C_1-C_8)$alkylene, O, S and $S(O)_n$, wherein the integer n is 1 or 2; and Z is selected from N and $C(R^8)$. $R^1$ and $R^2$ are independently selected from H, halogen, CN, $CO_2R'$, CONR'R", $(C_1-C_8)$alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from N, O and S, wherein R' and R" are independently selected from H, $(C_1-C_8)$alkyl and aryl. When R' and R" are attached to nitrogen, they may be combined with the nitrogen atom to form a 5-, 6-, or 7-membered ring. $R^3$, $R^4$ and $R^8$ are independently selected from H, halogen, CN, OH, $(C_1-C_8)$alkyl, heteroalkyl, aryl, heteroaryl, $O(C_1-C_8)$alkyl, $N(R^6)(R^7)$ and $OR^9$; $R^5$ is selected from H, $(C_1-C_8)$alkyl, heteroalkyl, aryl and heteroaryl; $R^6$ and $R^7$ are independently selected from H, $(C_1-C_8)$alkyl, heteroalkyl, aryl and heteroaryl; and $R^9$ is selected from $(C_1-C_8)$alkyl, heteroalkyl and haloalkyl.

Preferred compounds useful in the present compositions are those of formula I in which W is selected from substituted naphthyl, pyridyl quinolyl, $(C_1-C_8)$alkyl, heteroalkyl, cycloalkyl and heterocycloalkyl; X is selected from $N(R^5)$, S, O, $C(R^3)=C(R^4)$, $N=C(^4)$, and optionally, when Z is N, X can be $C(R^6)(R^7)$; Y is selected from a bond, $N(R^5)$, $N(R^5)-(C_1-C_8)$alkylene, O, S and $S(O)_n$, wherein the integer n is 1 or 2; and Z is selected from N and $C(R^8)$. $R^1$ and $R^2$ are independently selected from H, halogen, CN, $CO_2R^1$, CONR'R", $(C_1-C_8)$alkyl, heteroalkyl, aryl, heteroaryl, $N(R^6)(R^7)$, $OR^9$ and optionally, $R^1$ and $R^2$ combine to form a 5- to 8-membered ring containing from 0 to 3 heteroatoms selected from N, O and S, wherein R' and R" are independently selected from H, $(C_1-C_8)$alkyl and aryl. When R' and R" are attached to nitrogen, they may be combined with the nitrogen atom to form a 5-, 6-, or 7-membered ring. $R^3$, $R^4$ and $R^8$ are independently selected from H, halogen, CN, OH, $(C_1-C_8)$alkyl, heteroalkyl, aryl, heteroaryl, $O(C_1-C_8)$alkyl, $N(R^6)(R^7)$ and $OR^9$; $R^5$ is selected from H, $(C_1-C_8)$alkyl, heteroalkyl, aryl and heteroaryl; $R^6$ and $R^7$ are independently selected from H, $(C_1-C_8)$alkyl, heteroalkyl, aryl and heteroaryl; and $R^9$ is selected from $(C_1-C_8)$alkyl, heteroalkyl and haloalkyl.

Additional compounds useful in the present invention are those having the general formula:

$$Ar^1-X-Ar^2 \quad (II)$$

In formula II, the symbols $Ar^1$ and $Ar^2$ each independently represent a substituted or unsubstituted aryl, substituted or unsubstituted heteroaryl, or a substituted or unsubstituted fused aryl-heterocyclic ring system. The letter X represents a linking group selected from the group consisting of —N(R)—, —C(O)S—, —CH=CHSO$_2$— and —SO$_2$N(R)— wherein R is H or a substituted or unsubstituted $(C_1-C_8)$alkyl group. The linking group can be in either orientation relative to the $Ar^1$ and $Ar^2$ moieties. For example, the above general formula is meant to include both $Ar^1$—SO$_2$—NH—$Ar^1$ and $Ar^1$—NH—SO$_2$—$Ar^2$.

Returning to formula II above, in one group of preferred embodiments, $Ar^1$ is a substituted or unsubstituted heteroaryl group. Preferably $Ar^1$ is a substituted or unsubstituted 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, or 6-quinolyl group. More preferably, $Ar^1$ is a substituted or unsubstituted thiazolyl, thienyl, benzoxadiazolyl or oxazolyl group.

In another group of preferred embodiments, $Ar^2$ is a substituted or unsubstituted aryl group. More preferably, $Ar^2$ is a substituted or unsubstituted phenyl or naphthyl group. For those embodiments in which $Ar^2$ is a substituted aryl group, there will preferably be from 1 to 4 substituents, independently selected from halogen, hydroxy, $(C_1-C_4)$alkyl, $(C_1-C_4)$alkoxy, $(C_1-C_4)$alkylthio, $(C_1-C_4)$haloalkyl, $(C_1-C_4)$haloalkoxy, nitro, cyano, $(C_1-C_4)$acyl, amino, $(C_1-C_4)$alkylamino, and di$(C_1-C_4)$alkylamino. More preferably, there will be 1 to 3 substituents independently selected from halogen, $(C_1-C_4)$haloalkyl, $(C_1-C_4)$haloalkoxy, nitro, cyano and $(C_1-C_4)$acyl. In the most preferred embodiments, $Ar^2$ is a substituted or unsubstituted phenyl or naphthyl group. The substituted phenyl and napthyl groups will preferably have from 1 to 3 substituents independently selected from halogen, $(C_1-C_4)$haloalkyl, $(C_1-C_4)$haloalkoxy, nitro, cyano and $(C_1-C_4)$acyl.

In another group of preferred embodiments, $Ar^1$ and $Ar^2$ are each members independently selected from the group consisting of:

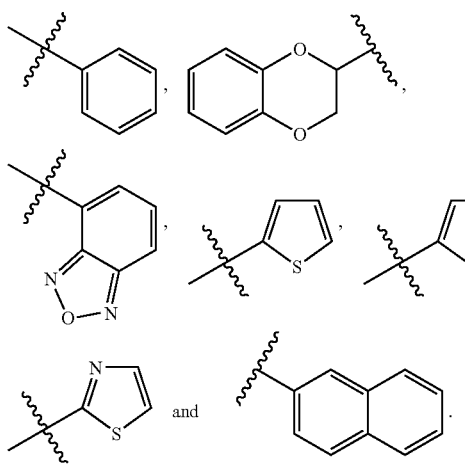

Further preferred are those embodiments in which $Ar^1$ is selected from substituted or unsubstituted phenyl or 2-naphthyl and $Ar^2$ is selected from substituted or unsubstituted

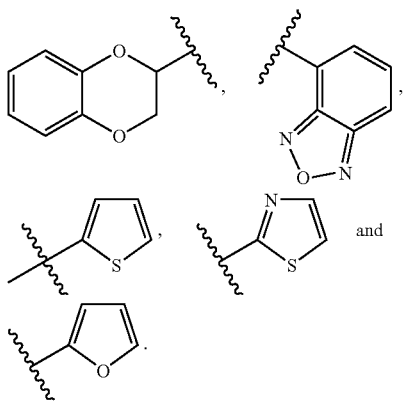

In the most preferred embodiments, the compounds used in the present compositions are selected from:

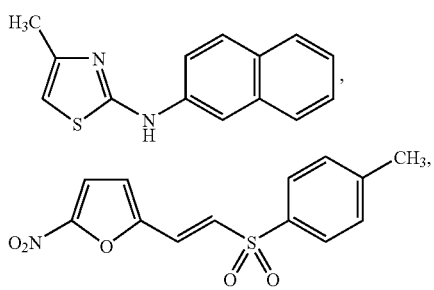

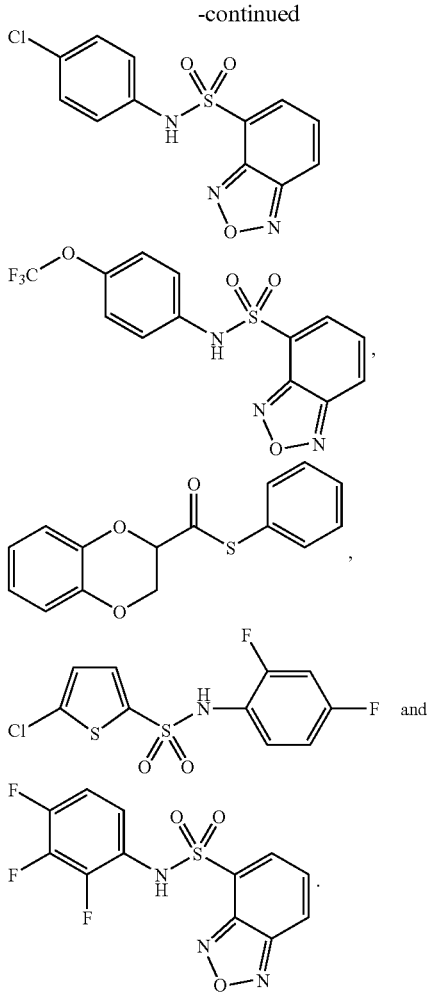

Preparation of CCR4 Modulators of Formula II

A number of compounds useful as modulators of CCR4 signalling can be obtained from commercial sources such as Maybridge Chemical Co. and Aldrich Chemical Co. (Milwaukee, Wis., USA).

Other compounds can be prepared using conventional methods. For example, Scheme I illustrates the preparation of diarylsulfonamides (certain compounds of formula II).

Scheme 1

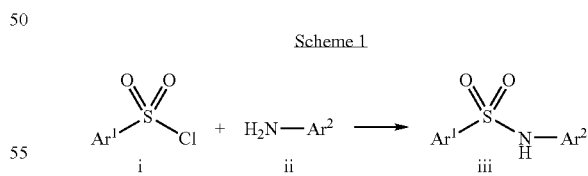

In this scheme, an aryl (or heteroaryl) sulfonyl chloride i can be combined with a suitable aryl (or heteroaryl) amine ii to provide the target sulfonamides iii. The starting sulfonyl chlorides are typically prepared in one step from a sulfonic acid using a chlorinating agent such as $POCl_3$ or $SOCl_2$. Similarly, starting arylamines ii are available from commercial sources or can be prepared in one step from the corresponding nitroaryl compounds.

In addition to the compounds provided above (of Formula I and Formula II), compositions for modulating chemokine receptor activity in humans and animals will typically contain a pharmaceutical carrier or diluent.

"Modulation" of chemokine receptor activity, as used herein in its various forms, is intended to encompass antagonism, agonism, partial antagonism and/or partial agonism of the activity associated with a particular chemokine receptor, preferably the CCR4 receptor. The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically active compounds as noted herein which are usually applied in the treatment of the above mentioned pathological conditions.

Methods of Treating CCR4-Mediated Conditions or Diseases

In yet another aspect, the present invention provides methods of treating or preventing a CCR4-mediated condition or disease by administering to a subject having such a condition or disease, a therapeutically effective amount of any compound of formula I above (e.g., without provisos) or a compound of formula II. Preferred compounds for use in the present methods are those compounds provided above as preferred embodiments, as well as compounds specifically exemplified in the Examples below, and provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR4-mediated condition or disease" and related phrases and terms refer to a condition or disease characterized by inappropriate, e.g., less than or greater than normal, CCR4 functional activity. Inappropriate CCR4 functional activity might arise as the result of CCR4 expression in cells which normally do not express CCR4, increased CCR4 expression (leading to, e.g.; inflammatory and immunoregulatory disorders and diseases) or decreased CCR4 expression. Inappropriate CCR4 functional activity might also arise as the result of TARC and/or MDC secretion by cells which normally do not secrete TARC and/or MDC, increased TARC and/or MDC expression (leading to, e.g., inflammatory and immunoregulatory disorders and diseases) or decreased TARC and/or MDC expression. A CCR4-mediated condition or disease may be completely or partially mediated by inappropriate CCR4 functional activity. However, a CCR4-mediated condition or disease is one in which modulation of CCR4 results in some effect on the underlying condition or disease (e.g., a CCR4 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated or prevented with the present compounds and compositions. In one group of embodiments, diseases or conditions, including chronic diseases, of humans or other species can be treated with inhibitors of CCR4 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

In another group of embodiments, diseases or conditions can be treated with agonists of CCR4 function. Examples of diseases to be treated with CCR4 agonists include cancers, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Preferably, the present methods are directed to the treatment of diseases or conditions selected from allergic diseases, psoriasis, atopic dermatitis and asthma.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat inflammatory conditions and diseases, including allergic diseases, psoriasis, atopic dermatitis and asthma, and those pathologies noted above.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with an analgesic listed above; a potentiator such as caffeine, an H2-antagonist (e.g., ranitidine), simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine.

Likewise, compounds and compositions of the present invention may be used in combination with other drugs that are used in the treatment, prevention, suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients or therapeutic agents, in addition to a compound of the present invention. Examples of other therapeutic agents that may be combined with a compound of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR1, CCR2, CCR3, CCR5, CCR6, CCR8 and CCR10; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon β-1α (Avonex®), azathioprine (Imurek®, Imuran®), glatiramer acetate (Capoxone®), a glucocorticoid (e.g., prednisolone) and cyclophosphamide (t) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In still other particularly preferred embodiments, the present methods are directed to the treatment of allergic diseases, wherein the compound of the invention is administered either alone or in combination with a second therapeutic agent, wherein said second therapeutic agent is an antihistamine. When used in combination, the practitioner can administer a combination of the therapeutic agents, or administration can be sequential.

In yet other particularly preferred embodiments, the present methods are directed to the treatment of psoriasis wherein the compound of the invention is used alone or in combination with a second therapeutic agent selected from a corticosteroid, a lubricant, a keratolytic agent, a vitamin $D_3$ derivative, PUVA and anthralin.

In particularly preferred embodiments, the present methods are directed to the treatment of atopic dermatitis using a compound of the invention either alone or in combination with a second therapeutic agent selected from a lubricant and a corticosteroid.

In particularly preferred embodiments, the present methods are directed to the treatment of asthma using a compound of the invention either alone or in combination with a second therapeutic agent selected from a β2-agonist and a corticosteroid.

Method of Evaluating Putative CCR4 Modulators

In yet another aspect, the present invention includes methods to evaluate putative specific agonists or antagonists of CCR4 function. Accordingly, the present invention is directed to the use of these compounds in the preparation and execution of screening assays for compounds which modulate the function of the CCR4 chemokine receptor. For example, the compounds of this invention are useful for isolating receptor mutants, which are excellent screening tools for potent compounds. Furthermore, the compounds of this invention are useful in establishing or determining the binding site of other compounds to the CCR4 chemokine receptor, e.g., by competitive inhibition. The compounds of the instant invention are also useful for the evaluation of putative specific modulators of the CCR4 chemokine receptor, relative to other chemokine receptors including CCR1, CCR2, CCR2A, CCR2B, CCR3, CCR5, CCR6, CCR8, CCR10, CXCR3 and CXCR4. One of skill in the art will appreciate that thorough evaluation of specific agonists and antagonists of the above chemokine receptors has been hampered by the lack of availability of non-peptidyl (metabolically resistant) compounds with high binding affinity for these receptors. The compounds provided herein are particularly useful in this context.

Combinatorial libraries of putative CCR4 agonists or antagonists can be screened for pharmacological activity in in vitro or in vivo assays. Conventionally, new chemical entities with useful properties are generated by identifying a chemical compound (called a "lead compound") with some desirable property or activity, e.g., CCR4 chemokine receptor modulation activity, creating variants of the lead compound, and evaluating the properties and activities of those variant compounds. However, the current trend is to shorten the time scale for all aspects of drug discovery. Because of the ability to test large numbers of compounds quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks", such as reagents. For example, a linear combinatorial chemical library, such as a polypeptide (e.g., mutein) library, is formed by combining a set of chemical building blocks called amino acids in very possible way for a given compound length (i.e., the number of amino acids in a polypeptide compound). Millions of chemical compounds can be synthesized through such combinatorial mixing of chemical building blocks (Gallop et. al. (1994) *J. Med. Chem.* 37(9):1233-1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.* 37:487-493, Houghton et. al. (1991) *Nature* 354: 84-88), peptoid libraries (PCT Publication No WO 91/19735), encoded peptide libraries (PCT Publication WO 93/20242), random bio-oligomer libraries (PCT Publication WO 92/00091), benzodiazepine libraries (U.S. Pat. No. 5,288,514), libraries of diversomers, such as hydantoins, benzodiazepines and dipeptides (Hobbs et. al. (1993) *Proc. Nat. Acad. Sci. USA* 90:6909-6913), vinylogous polypeptide libraries (Hagihara et al. (1992) *J. Amer. Chem. Soc.* 114:6568), libraries of nonpeptidyl peptidomimetics with a Beta-D-Glucose scaffolding (Hirschmann et al. (1992) *J. Amer. Chem. Soc.* 114:9217-9218), analogous organic syntheses of small compound libraries (Chen et. al. (1994) *J. Am. Chem. Soc.* 116:2661), oligocarbamate libraries (Cho et al. (1993) *Science* 261:1303) and/or peptidyl phosphonate libraries (Campbell et al. (1994) *J. Org. Chem.* 59:658). See, generally, Gordon et al. (1994) *J. Med. Chem.* 37:1385-1401, nucleic acid libraries (see, e.g., Stratagene Corp.), peptide nucleic acid libraries (see, e.g., U.S. Pat. No. 5,539,083), antibody libraries (see, e.g., Vaughn et. al. (1996) *Nature Biotechnology* 14(3):309-314), and PCT/US96/10287), carbohydrate libraries (see, e.g., Liang et al. (1996) *Science* 274:1520-1522, and U.S. Pat. No. 5,593, 853), and small organic molecule libraries (see, e.g., benzodiazepines, Baum (1993) *C&EN* January 18, page 33 and U.S. Pat. No. 5,288,514; isoprenoids, U.S. Pat. No. 5,549, 974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (see, e.g., 357 MPS, 390 MPS, Advanced Chem Tech, Louisville Ky.; Symphony, Rainin, Woburn Mass.; 433A Applied Biosystems, Foster City Calif.; 9050 Plus, Millipore, Bedford, Mass.).

A number of well known robotic systems have also been developed for solution phase chemistries. These systems includes automated workstations like the automated synthesis apparatus developed by Takeda Chemical Industries, LTD. (Osaka, Japan) and many robotic systems utilizing robotic arms (Zymate II, Zymark Corporation, Hopkinton Mass.; Orca, Hewlett-Packard, Palo Alto Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see e.g., ComGenex, Princeton N.J.; Asinex, Moscow, Russia; Tripos, Inc., St. Louis Mo.; ChemStar, Ltd, Moscow, Russia; 3D Pharmaceuticals, Exton Pa.; Martek Biosciences, Columbia Md.; etc.).

High throughput assays for the presence, absence, quantification, or other properties of particular compounds may be used to test a combinatorial library that contains a large number of potential therapeutic compounds (potential modulator compounds). The assays are typically designed to screen large chemical libraries by automating the assay steps and providing compounds from any convenient source to the assays, which are typically run in parallel (e.g. in microtiter formats on microtiter plates in robotic assays). Preferred assays detect enhancement or inhibition of CCR4 receptor function.

High throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start-up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Other Evaluation Assays for CCR4 Modulators

A variety of assays can be used to evaluate the compounds provided herein, including CCR4 binding assays, CCR4 signalling assays, chemotaxis assays, and other assays of cellular response.

In a suitable assay, a CCR4 protein (whether isolated or recombinant) is used which has at least one property, activity or functional charateristic of a mammalian CCR4 protein. The property can be a binding property (to, for example, a ligand or inhibitor), a signalling activity (e.g., activation of a mammalian G protein, induction of rapid and transient increase in the concentration of cytosolic free calcium $[Ca^{++}]_i$), cellular response function (e.g., stimulation of chemotaxis or inflammatory mediator release by leukocytes), and the like.

In one embodiment, a composition containing a CCR4 protein or variant thereof is maintained under conditions suitable for binding. The CCR4 receptor is contacted with a putative agent (or a second composition containing at least one putative agent) to be tested, and binding is detected or measured.

In one group of preferred embodiments, the assay is a cell-based assay and cells are used which are stably or transiently transfected with a vector or expression cassette having a nucleic acid sequence which encodes the CCR4 receptor. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., TARC or MDC) as a competitor.

In other embodiments, binding inhibition assays can be used to evaluate the present compounds. In these assays, the compounds are evaluated as inhibitors of ligand binding using, for example, TARC or MDC. In this embodiment, the CCR4 receptor is contacted with a ligand such as TARC or MDC and a measure of ligand binding is made. The receptor is then contacted with a test agent in the presence of a ligand (e.g., TARC or MDC) and a second measurement of binding is made. A reduction in the extent of ligand binding is indicative of inhibition of binding by the test agent. The binding inhibition assays can be carried out using whole cells which express CCR4, or a membrane fraction from cells which express CCR4.

The binding of a G protein-coupled receptor by, for example, an agonist, can result in a signalling event by the receptor. Accordingly, signalling assays can also be used to evaluate the compounds of the present invention and induction of signalling function by an agent can be conitored using any suitable method. For example, G protein activity, such as hydrolysis of GTP to GDP, or later signalling events triggered by receptor binding can be assayed by known methods (see, for example, PCT/US97/15915; Neote, et al., Cell, 72:415-425 (1993); Van Riper, et al., J. Exp. Med., 177:851-856 (1993) and Dahinden, et al., J. Exp. Med., 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. Suitable assays are described in PCT/US97/15915; Springer, et al., WO 94/20142; Berman et al., Immunol. Invest., 17:625-677 (1988); and Kavanaugh et al., J. Immunol., 146:4149-4156 (1991)).

The compounds provided herein can also be evaluated using models of inflammation to assess the ability of the compound to exert an effect in vivo. Suitable models are described as follows: a sheep model for asthma (see, Weg, et al., J. Exp. Med., 177:561 (1993)); and a rat delayed-type hypersensitivity model (see Rand, et al., Am. J. Pathol., 148:855-864 (1996)). Another useful model for evaluating the instant compounds is the experimental autoimmune encephalomyelitis (EAE) model for multiple sclerosis, which probes chemokine receptor expression and function (see, Ransohoff, et al., Cytokine Growth Factor Rev., 7:3546 (1996), and Karpus, et al., J. Immunol. 161:2667-2671 (1998)).

In addition, leukocyte infiltration assays can also be used to evaluate a compound (see, Van Damme, et al., J. Exp. Med. 176:59-65 (1992); Zachariae, et al., J. Exp. Med. 171:2177-2182 (1990); and Jose, et al, J. Exp. Med. 179: 881-887 (1994)).

The following examples are offered to illustrate, but not to limit the claimed invention.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

General Procedures

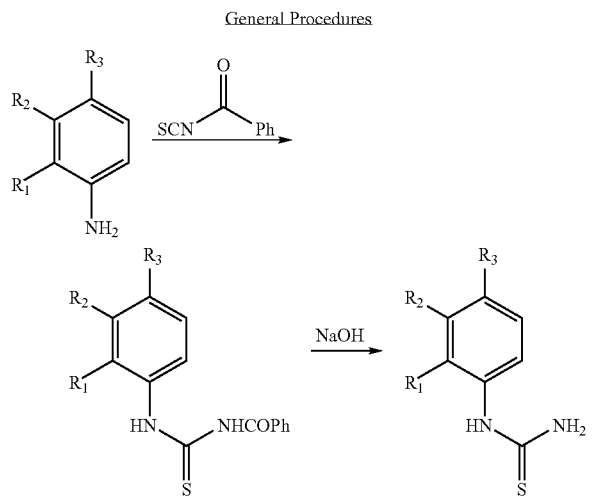

General Procedures

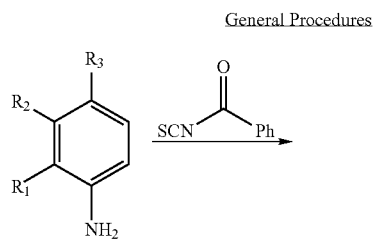

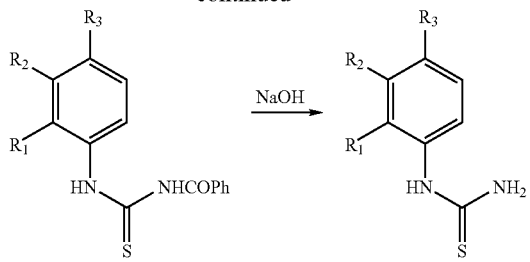

General Procedure for Preparing Aryl Thioureas

To a solution of aryl amine (4.1 mmol) in dry acetone (30 mL) at room temperature was added dropwise benzoyl-isothiocyanate (0.56 mL, 4.5 mmol). After 1 h, the reaction mixture was concentrated in vacuo to afford a solid compound, which was triturated with 50% aqueous ethanol (50 mL) to dissolve inorganic materials. The crude product was stirred with 20 mL of 10% NaOH at 98° C. for 10 min. After cooling, the basic solution was neutralized by adding 10% HCl solution. The precipitate was filtered and then washed with water.

General Procedure for Preparing 2-Amino-4-Alkyl-Substituted Thiazoles

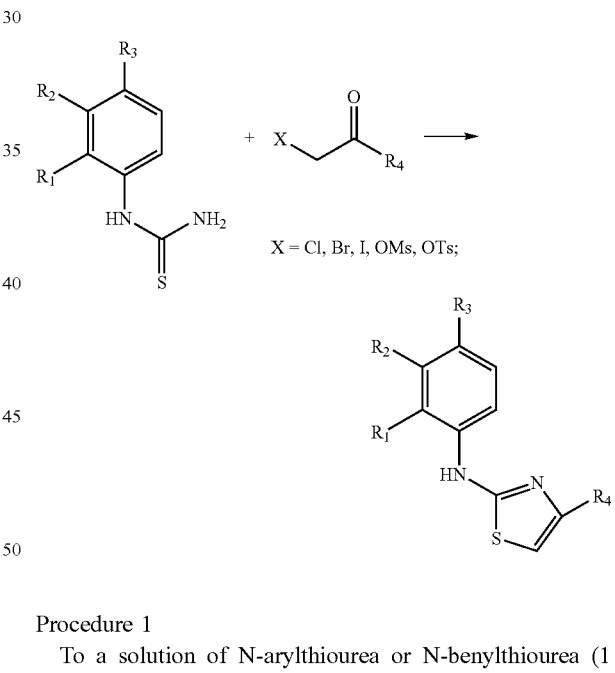

Procedure 1

To a solution of N-arylthiourea or N-benylthiourea (1 mmol) in methanol (5 mL) at room temperature was added α-haloketone (1.05 mmol). The reaction mixture was refluxed for 3 h and then concentrated in vacuo. The crude compound was then recrystalized with ethyl ether and methylene chloride to afford 2-aminothiazole as the salt form.

Procedure 2

To a boiling suspension of N-arylthiourea (1.0 mmol) and MgSO$_4$ (60 mg) in acetone (6.0 mL) was added a solution of a-haloketone (1.1 mmol) in acetone (1.0 mL) dropwise. The reaction mixture was refluxed for 2 to 8 h. The mixture was then cooled to room temperature, poured into a saturated solution of brine (5 mL). The solution was then basified with concentrated NH₄OH aqueous solution, diluted with water (5 mL) and then extracted with EtOAc (2×20 mL). The organic layers were combined, dried over anhydrous MgSO₄ and concentrated in vacuo. The crude product was purified by silica gel flash column chromatography (ethyl acetate and hexanes).

In some cases, the desired thiazole products were precipitated from reaction solution. The isolation was then carried out by filtration through a Bückner funnel and washed the solid with acetone. The final products were isolated as the salt forms.

Example 1

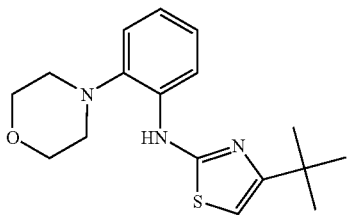

1

¹H NMR (400 MHz, CDCl₃): δ 7.4-7.5 (m, 1H), 7.3-7.4 (m, 2H), 7.2-7.3 (m, 1H), 6.17 (s, 1H), 4.04 (m, 4H), 2.96 (m, 4H), 1.47 (s, 9H); MS (ES+): 318.2 (M+H).

Example 2

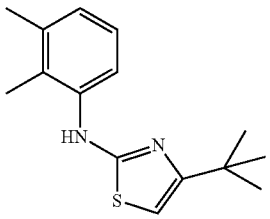

2

¹H NMR (400 MHz, CDCl₃): δ 11.2 (s, br, 1H), 7.1-7.2 (m, 3H), 6.04 (s, 1H), 2.35 (s, 3H), 1.57 (s, 3H), 1.44 (s, 9H). MS (ES+): 261.1 (M+H).

Example 3

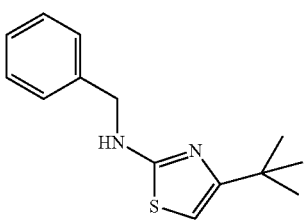

3

¹H NMR (400 MHz, CDCl₃): δ 10.1 (s, br, 1H), 7.3-7.4 (m, 5H), 6.01 (s, 1H), 4.51 (s, 2H), 1.39 (s, 9H). MS (ES+): 247.1 (M+H).

Example 4

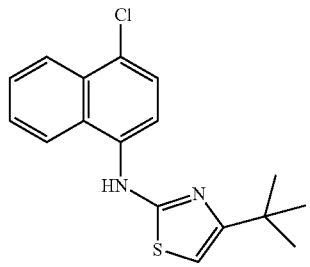

4

¹H NMR (400 MHz, CDCl₃): δ 12.0 (s, br, 1H), 8.3-8.4 (m, 2H), 7.7-7.8 (m, 2H), 7.63 (d, J=8.1 Hz, 1H), 7.53 (d, J=8.1 Hz, 1H), 6.13 (s, 1H), 1.44 (s, 9H). MS (ES+): 317.1 (M+H).

Example 5

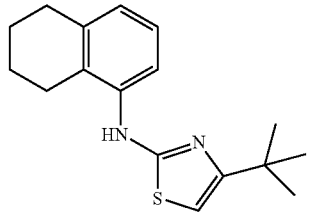

5

¹H NMR (400 MHz, CDCl₃): δ 7.1-7.2 (m, 3H), 6.14 (s, 1H), 2.82 (t, J=6 Hz, 2H), 2.77 (t, J=6 Hz, 2H), 1.8-1.9 (m, 4H), 1.41 (s, 9H). MS (ES+): 287.1 (M+H).

Example 6

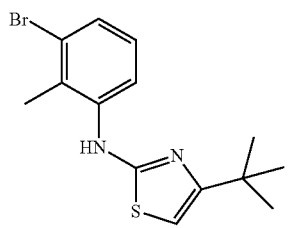

6

¹H NMR (400 MHz, CDCl₃): δ 11.46 (s, br, 1H), 7.60 (d, J=8 Hz, 1H), 7.36 (d, J=8 Hz, 1H), 7.17 (t, J=8 Hz, 1H), 6.11 (s, 1H), 2.54 (s, 3H), 1.44 (s, 9H). MS (ES+): 325.1 (M+H).

Example 7

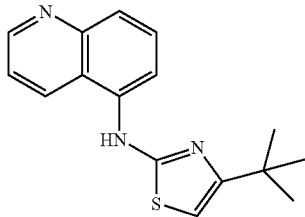

7

¹H NMR (400 MHz, CDCl₃): δ 9.34 (s, br, 1H), 9.23 (d, J=8.5 Hz, 1H), 8.49 (d, J=8.1 Hz, 1H), 7.9-8.1 (m, 3H), 6.23 (s, 1H), 1.46 (s, 9H). MS (ES+): 284.1 (M+H).

Example 8

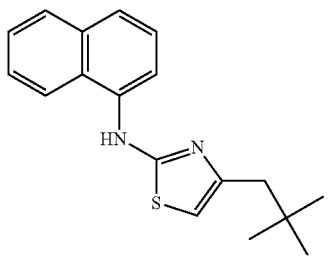

8

To a solution of 4,4-dimethyl-2-pentanone (0.25 mL, 1.7 mmol) in methanol (10 mL) was added bromine (0.09 mL, 1.7 mmol) in methanol (3 mL) dropwise at 0° C. The reaction mixture was warmed up from 0° C. to room temperature, and kept at room temperature for 1 h. 1-Naphthylthiourea (0.35 g, 1.7 mmol) was then added to the reaction mixture and refluxed for 3 h. The reaction mixture was concentrated in vacuo. The crude compound was recrystalized with ethyl ether and methylene chloride to afford 2-aminothiazole as the HBr salt. ¹H-NMR (400 MHz, CDCl₃): δ 8.12 (d, J=8.1 Hz, 1H), 7.8-8.0 (m, 2H), 7.1-7.7 (m, 4H), 6.04 (s, 1H), 2.76 (s, 2H), 1.44 (s, 9H). MS (ES+): 297.2 (M+H).

Example 9

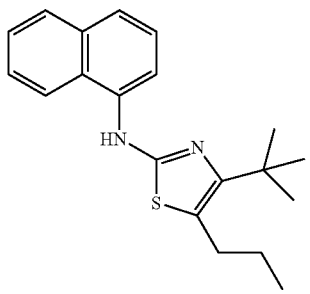

9

¹H NMR (400 MHz, CDCl₃): δ 12.6 (s, br, 1H), 8.41 (d, J=8.1 Hz, 1H), 7.91 (dd, J=8.1, 21 Hz, 2H), 7.5-7.7 (m, 4H), 2.73 (t, J=8 Hz, 2, 1.5-1.6 (m, 2H), 1.55 (s, 9H), 1.0 (t, J=8 Hz, 3H). MS (ES+): 325.2 (M+H).

Example 10

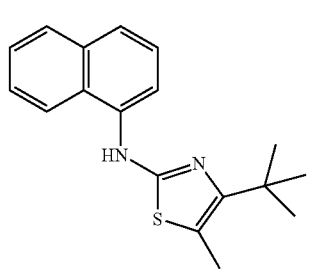

10

¹H NMR (400 MHz, CDCl₃): δ 13.6 (s, br, 1H), 8.12 (d, J=8.1 Hz, 1H), 7.91 (dd, J=8.1, 21 Hz, 2H), 7.4-7.6 (m, 4H), 2.27 (s, 3H), 1.49 (s, 9H). MS (ES+): 297.2 (M+H).

Example 11

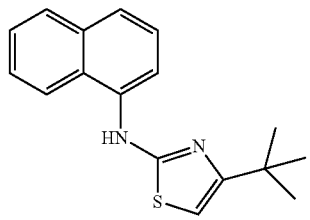

11

¹H NMR (400 MHz, CDCl₃): δ 11.02 (s, 1H), 8.09-8.07 (m, 1H), 7.92-7.89 (m, 1H), 7.82 (d, J=7.5 Hz, 1H), 7.69 (d, J=8.3 Hz, 1H), 7.58-7.53 (m, 2H), 7.50 (dd, J=7.8, 7.8 Hz, 1H), 6.21 (s, 1H), 1.37 (s, 9H); MS (ES+): 283.1 (M+H).

Example 12

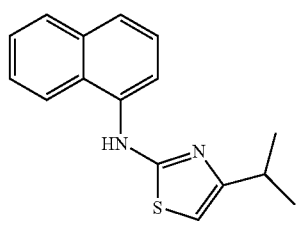

12

¹H NMR (400 MHz, CDCl₃): δ 8.10 (d, J=9.4 Hz, 1H), 7.91 (dd, J=9.4, 2.7 Hz, 1H), 7.73 (d, J=7.7 Hz, 2H), 7.55-7.28 (m, 3H), 6.14 (s, 1H), 2.95 (septet, J=6.9 Hz, 1H), 6.9 (d, J=6.9 Hz, 6H); MS (ES+) 269.1 (M+H).

Example 13

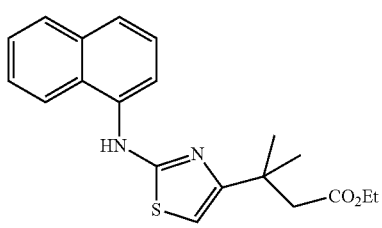

¹H NMR (400 MHz, CDCl₃): δ 8.06 (dd, J=6.3, 3.5 Hz, 1H), 7.92-7.89 (m, 1H), 7.81 (d, J=7.5 Hz, 1H), 7.69 (d, J=8.3 Hz, 1H), 7.53 (dd, J=6.3, 3.2 Hz, 2H), 7.49 (dd, J=7.8, 7.8 Hz, 1H), 6.25 (s, 1H), 4.09 (q, J=7.1 Hz, 2H), 2.72 (s, 2H), 1.46 (s, 6H), 1.21 (t, J=7.1 Hz, 3H); MS (ES+) 355.1 (M+H).

Example 14-15

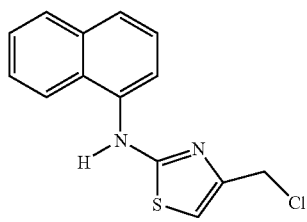

A mixture of 14 (70 mg, 0.22 mmol, prepared from 1,3-dichloroacetone and N-naphthylthiourea following general procedure 2) and diisopropylamine (129 mg, 1.0 mmol) in ethanol (1.5 mL) was stirred at reflux for 6 h. After evaporating ethanol the crude product was purified by HPLC to afford the desired product (TFA salt) as colorless liquid (33 mg, 40% yield). ¹H-NMR (400 MHz, CDCl₃): δ 11.1 (s, 1H), 8.05-8.03 (m, 1H), 7.96-7.94 (m, 1H), 7.87 (d, J=8.3, 1H), 7.69 (dd, J=8.3, 0.9 Hz, 1H), 7.65-7.59 (m, 2H), 7.53 (dd, J=7.8, 7.8 Hz, 1H), 7.06 (s, 1H), 4.37 (s, 2H), 3.00 (d, J=6.7 Hz, 4H), 2.20-2.11 (m, 2H), 1.09 (d, J=6.7 Hz, 12H). MS (ES+) 368.3 (M+H).

Examples 16-18

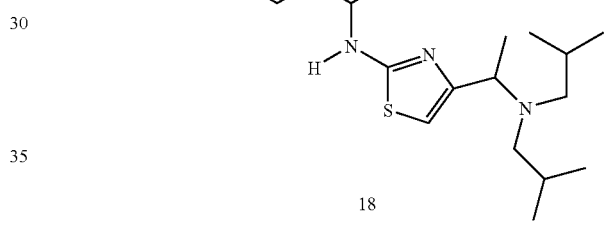

Example 16

Compound 16 was prepared from N-naphthylthiourea (606 mg, 3.0 mmol) and 1-bromo-2,3-butanedione (4.0 mmol) according to general procedure 2. This material was carried to the next step without further purification.

Example 17

To a stirred suspension of 4-acetoyl-2-naphthylamino thiazole (65 mg, 0.18 mmol) and iso-butylamine (53 mg, 0.72 mmol) in methanol (3 mL) was added a solution of sodium cyanoborohydride (30 mg) in methanol (1 mL) at 0° C. After stirring the mixture for 12 h, it was diluted with EtOAc (20 mL) and washed with water (2×5 mL). The organic layer was dried over MgSO4, filtered and concentrated in vacuo. The residue was purified by HPLC to give 4-iso-butylamino-2'-ethyl-2-naphthylaminothiazole (17) as white solid (27 mg, 45% yield).

Example 18

Compound 18 was prepared from 4-iso-butylamino-2'-ethyl-2-naphthylamino thiazole and iso-butylaldehyde according to the general procedure of reductive amination outlined above. Purification of the crude product by HPLC afforded the desired product as white solid (61 mg, 50% yield). $^1$H-NMR (400 MHz, CDCl$_3$): δ 7.97-7.95 (m, 1H), 7.83-7.81 (m, 1H), 7.68-7.62 (m, 2H), 7.47-7.45 (m, 2H), 7.39 (dd, J=7.8, 7.8 Hz, 1H), 6.64 (s, 1H), 4.53 (q, J=6.7 Hz, 1H), 2.92 (m, 2H), 2.66 (m, 2H), 1.96 (m, 2H), 1.59 (d, J=6.7 Hz, 3H), 0.94 (d, J=6.6 Hz, 6H), 0.80 (d, J=6.6 Hz, 6H); MS (ES+) 382.3 (M+H).

Example 19

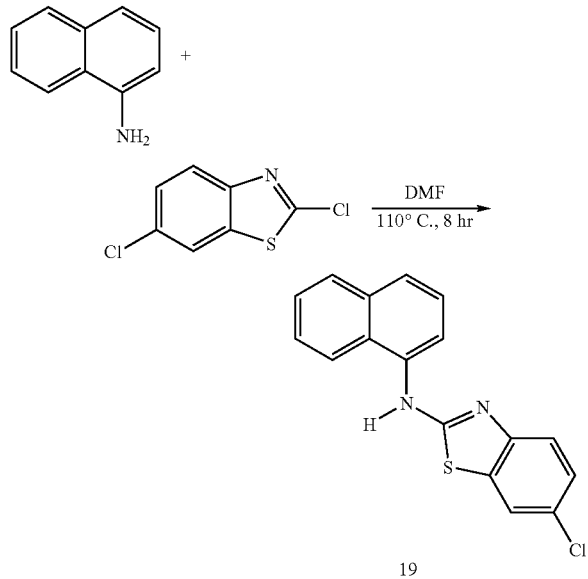

A mixture of 1-aminonaphthalene (2.0 mmol, 268 mg) and 2,6-dichlorobenzenethiazole (1.0 mmol, 203 mg) in DMF (3.0 mL) was heated at 110° C. for 8 h. The mixture was allowed to cool to room temperature, diluted with EtOAc (15.0 mL) and then extracted with H$_2$O (4×10 mL) to remove DMF. The organic layer was dried over anhydrous MgSO$_4$, filtered and concentrated in vacuo. The residue was purified by silica gel flash column chromatography (hexanes/EtOAc) to afford the desired product as yellow solid (124 mg, 40% yield). $^1$H-NMR (400 MHz, CDCl$_3$): δ 7.87-7.83 (m, 4H), 7.51-7.49 (m, 2H), 7.36-7.33 (m, 2H), 6.82 (dd, J=6.8, 1.5 Hz, 2H). MS (ES+) 311.0 (M+H).

Example 20

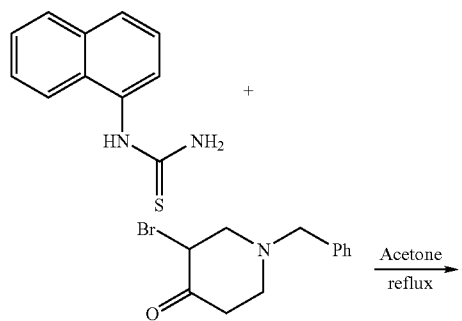

This compound was prepared from 1-benzyl-3-bromo-4-piperidone (which is synthesized from 1-benzyl-4-piperidone by regioselective bromination) and N-naphthylthiourea following a general procedure. Purification of the crude product by HPLC gave (20) as white solid (178 mg, 48% yield). $^1$H NMR (400 MHz, CDCl$_3$): δ 7.89 (d, J=9.1 Hz, 1H), 7.87 (d, J=8.4 Hz, 1H), 7.73-7.68 (m, 2H), 7.58-7.41 (m, 4H), 7.32-7.21 (m, 4H), 3.49 (s, 2H), 3.14 (s, 2H), 2.68 (t, J=5.4 Hz, 2H), 2.60 (t, J=5.4 Hz, 2H); MS (ES+) 372.2 (M+H).

Example 21

This example illustrates a CCR4 binding assay that can be used for evaluating the compounds of the present invention.

Detection of Radiolabelled TARC and/or MDC Binding to CCR4

$^{125}$I-labelled TARC and MDC are available from commercial sources (e.g., Amersham-Pharmacia or Perkin Elmer Life Sciences). All buffers and materials are available from commercial sources (e.g., Gibco BRL, Sigma). To measure binding of $^{125}$I-TARC or $^{125}$I-MDC to cells expressing CCR4 (e.g., CEM cells, available from the ATCC), the $^{125}$I-TARC or $^{125}$I-MDC is diluted to a concentration of approximately 200 pM in a buffered saline solution (e.g., RPMI supplemented with 0.5% bovine serum albumin), and added to an equal volume of a suspension of cells (e.g., CEM cells at 5×10$^6$ cells/mL). The resulting mixture is incubated for a period of time (e.g., 2 hours). The unbound $^{125}$I-TARC or $^{125}$I-MDC is separated from the cells by filtration, e.g., by passage through GF/B filter plate (Packard Biosciences) pre-treated with 0.3% polyethyleneimine (Sigma), using a Packard Filtermate 96 (Packard Biosciences). The amount of $^{125}$I-TARC or $^{125}$I-MDC retained with the cells on the filterplate is measured by adding a small amount of scintillation fluid (e.g., 50 μL of Microscint-20, obtained from Packard Biosciences), and reading scintillation on appropriate detection equipment, e.g., a Packard TopCount 383 (Packard Biosciences).

Non-specific binding of $^{125}$I-TARC or $^{125}$I-MDC can be estimated by measuring the amount of $^{125}$I-TARC or $^{125}$I-MDC retained with the cells on the filterplate when the assay is performed in the presence of a large excess of unlabelled TARC or MDC.

Inhibition of $^{125}$I-TARC or $^{125}$I-MDC binding to CCR4 is defined as a decrease in the retention of $^{125}$I-TARC or $^{125}$I-MDC to the cells on the filterplate.

The assay described above varies only moderately from standardly used procedures, e.g., Imai et al. (1997) *J. Biol. Chem.* 272:15036-15042, Imai et al. (1998) *J. Biol. Chem.* 273:1764-1768.

TABLE 1

CCR4 antagonist activity for compounds of the invention (inhibition of $^{125}$I-TARC binding).

| Compound | IC$_{50}$ (nM) |
|---|---|
| 12 | + |
| 2 | + |
| 11 | + |
| 4 | ++ |
| 9 | + |
| 10 | + |
| 1 | ++ |
| 3 | ++ |
| 13 | + |
| 5 | + |
| 19 | ++ |
| 8 | + |
| 15 | + |
| 6 | + |
| 18 | + |
| 7 | ++ |
| 20 | + |

+ denotes IC$_{50}$ > 1000 nM
++ denotes IC$_{50}$ < 1000 nM

Example 22

This example illustrates additional screening procedures used in characterizing the compounds of the present invention.

Source plates of chemical libraries were obtained from commercial vendors and contained individual compounds at 5 mg/mL in DMSO, or in some instances, at 1 mg/mL. From these, multiple compound plates containing 10 compounds in each well were made, and these were diluted in 20% DMSO to a concentration of 50 µg/mL (10 µg/mL for those beginning at 1 mg/mL). An aliquot of 20 µL of each mixture was put into the test plates, which were stored frozen until use.

A CCR4 expressing stable transfectant cell line was prepared using current standard molecular biological methods. The CCR4 transfectants were cultured in IMDM-5% FBS, and harvested when the concentration was between 0.5-1.0×10$^6$ cells/ml. The cells were centrifuged and resuspended in assay buffer (20 mM HEPES pH 7.1, 140 mM NaCl, 1 mM CaCl$_2$, 5 mM MgCl$_2$, and with 0.2% bovine serum albumin) to a concentration of 5.6×10$^6$ cells/ml. To set up the screening assays, first 0.09 ml of cells was added to the assay plates containing the compounds. (For a final compound concentration of 1-5 µg/ml each [~2-10 µM]). Then 0.09 ml of $^{125}$I labeled MDC or TARC diluted in assay buffer (final concentration ~50 pM, with ~30,000 cpm per well) was added. The plates were sealed and incubated for approximately 3 hours at 4° C. on a shaker platform. The assay plates were harvested using Packard filter plates, pre-soaked in 0.3% PEI (polyethyleneimine) solution, on a Packard vacuum cell harvester. Scintillation fluid (50 µl) was added to all wells and the plates were sealed and counted in a Top Count scintillation counter. Control wells containing either diluent only (for total counts) or excess MDC or TARC (1 µg/ml, for non-specific binding) were used to calculate the percent of total inhibition for each set of compounds. Further tests on individual compounds were carried out in the same manner. IC$_{50}$ values are those concentrations required to reduce the binding of labeled MDC or TARC to the receptor by 50%.

The calcium mobilization experiments were performed by labeling the human T-cell line CEM with INDO-1 dye (45 min at room temperature), washing with PBS, and resuspending into flux buffer (HBSS with 1% fetal bovine serum). For each test, 1×10$^6$ cells were incubated at 37° C. in the cuvette of a PTI spectrometer, and the ratio of 410/490 nm emission plotted over time (typically 2-3 minutes), with compounds added at 5 seconds, followed by MDC, TARC or other chemokines.

Chemotaxis assays were performed using 5µ filter plates (Neuroprobe) with the chemoattractant (MDC, TARC, or SDF) placed in the lower chamber, and a cell suspension of 100,000 CEM cells in the upper chamber. The assays were incubated 1-2 hours at 37° C., and the number of cells in the lower chamber quantified by the CyQuant assay (Molecular Probes).

Results are provided in Figures.

Example 23

This example describes a procedure to evaluate the efficacy of CCR4 antagonists for treatment of septic shock.

An animal model of endotoxic shock can be induced by injecting rodents with lipopolysaccharide (LPS). Three series of mouse groups, comprising 15 mice per group, are treated with an intra-peritoneal injection of an L.D. (lethal dose)-90 of LPS (precise dose requires titration of the particular batch of lipopolysaccharide in the actual mouse colony in use to determine a re-producible dose of LPS that produces 90% mortality in mice). One series of mice additionally receives phosphate buffered saline (PBS) and Tween 0.5% i.p. 30 minutes before LPS administration. A second series consists of groups of mice receiving different doses of the CCR4 antagonist(s) given either intra-peritoneally, intra-venously, sub-cutaneously, intramuscularly, orally, or via any other mode of administration 30 minutes before, or concurrently with, LPS administration. A third series of mice, serving as positive control, consists of groups treated with either mouse IL-10 i.p., or anti-TNF antibodies i.p., 30 minutes before LPS administration.

Mice are monitored for death for 72 hours following the LPS injection.

Example 24

This example describes a procedure to evaluate the efficacy of CCR4 antagonists for treatment of asthma.

An animal model of asthma can be induced by sensitizing rodents to an experimental antigen (e.g. OVA) by standard immunization, and then subsequently introducing that same antigen into the rodents lung by aerosolization. Three series of rodent groups, comprising 10 rodents per goup, are actively sensitized on Day 0 by a single intraperitoneal injection with 100 ug OVA in phosphate-buffered saline (PBS), along with an IgE-selective adjuvant e.g. aluminum hydroxide. At 11 days after sensitization, at the peak of their IgE response, the animals are placed in a Plexiglas chamber and challenged with aerosolized OVA (1%) for 30 minutes using the ultrasonic nebulizer (De Vilbliss). One series of mice additionally receives phosphate buffered saline (PBS) and Tween 0.5% i.p. at the initial sensitization, and at different dosing schedules thereafter, up until the aerosolized OVA challenge. A second series consists of groups of mice receiving different doses of the CCR4 antagonist(s) given either intra-peritoneally, intra-venously, sub-cutaneously, intramuscularly, orally, or via any other mode of administration at the initial sensitization, and at different dosing schedules thereafter, up until the aerosolized OVA challenge. A third series of mice, serving as positive control, consists of groups treated with either mouse IL-10 i.p., anti-IL4 antibodies i.p., or anti-IL5 antibodies i.p. at the initial sensitization, and at different dosing schedules thereafter, up until the aerosolized OVA challenge.

Animals were subsequently analyzed at different time points after the aerosolized OVA challenge for pulmonary function, cellular infiltrates in bronchoalveolar lavage (BAL), histological examination of lungs, and measurement of serum OVA-specific IgE titers.

Example 25

This example describes a procedure to evaluate the efficacy of CCR4 antagonists for augmenting protective immunity against viruses, bacteria and parasites.

Protective immunity to microbial pathogens is frequently mediated by Th1 regulatory T cells. Since CCR4 antagonists are likely inhibitors of Th2 regulatory cells, they may alter the cross regulation that normally exists between Th1 and Th2 cells, and potentiate Th1 cells, thereby augmenting protection against infectious disease. Three series of mouse groups, comprising 15 mice per group, are infected with the intracellular parasite *Leishmania major* (*L. major*) by injecting *L. major* promastigotes sub-cutaneously into their left hind footpads. Four weeks after infection, the animals are challenged with either Leishmania freeze-thawed antigen, or PBS as a negative control, in the contra-lateral footpad. One series of mice additionally receives phosphate buffered saline (PBS) and Tween 0.5% i.p. at the initial sensitization, and at different dosing schedules thereafter, up until the Leishmania antigen challenge. A second series consists of groups of mice receiving different doses of the CCR4 antagonist(s) given either intra-peritoneally, intra-venously, sub-cutaneously, intramuscularly, orally, or via any other mode of administration at the initial sensitization, and at different dosing schedules thereafter, up until the Leishmania antigen challenge. A third series of mice, serving as positive control, consists of groups treated with either mice IL-12, anti-IL4 antibodies i.p., or anti-IL5 antibodies i.p. at the initial sensitization, and at different dosing schedules thereafter, up until the Leishmania antigen challenge.

Over the next 48 hours, footpad swelling, caused by a Delayed-Type Hypersensitivity reaction to the Leishmania antigen challenge, is monitored with a metric caliper. The response of draining lymph node T cells to Leishmania antigen stimulation in vitro is also measured, both at the level of proliferation, cytokine production, and other phenotypic criteria.

Example 26

This example describes a procedure to evaluate the efficacy of CCR4 antagonists for treatment of rheumatoid arthritis.

An animal model of rheumatoid arthritis can be induced in rodents by injecting them with type II collagen in selected adjuvants. Three series of rodent groups consisting 15 genetically-susceptible mice or rats per group are injected sub-cutaneously or intra-dermally with type II collagen emulsified in Complete Freund's Adjuvant at days 0 and 21. One series of rodents additionally receives phosphate buffered saline (PBS) and Tween 0.5% i.p. at the initial sensitization, and at different dosing schedules thereafter. A second series consists of groups of rodents receiving different doses of the CCR4 antagonist(s) given either intra-peritoneally, intra-venously, sub-cutaneously, intra-muscularly, orally, or via any other mode of administration at the initial sensitization, and at different dosing schedules thereafter. A third series of rodents, serving as positive control, consists of groups treated with either mouse IL-10 i.p., or anti-TNF antibodies i.p. at the initial sensitization, and at different dosing schedules thereafter.

Animals are monitored from weeks 3 til 8 for the development of swollen joints or paws, and graded on a standard disease severity scale. Disease severity is confirmed by histological analysis of joints.

Example 27

This example describes a procedure to evaluate efficacy of CCR4 antagonists for treatment of Systemic Lupus Erythematosus (SLE).

Female NZB/W F1 mice spontaneously develop an SLE-like pathology commencing at 6 months of age that is characterized by proteinuria, serum autoantibodies, glomerulonephritis, and eventually death. Three series of NZB/W mouse groups comprising 20 mice per group are tested for efficacy of CCR antagonist(s) as follows: One series of mice additionally receives phosphate buffered saline (PBS) and Tween 0.5% i.p. soon after weaning, and thereafter at varying dosing schedules. A second series consists of groups of mice receiving different doses of the CCR4 antagonist(s) given either intra-peritoneally, intravenously, sub-cutaneously, intra-muscularly, orally, or via any other mode of administration soon after weaning, and thereafter at varying dosing schedules. A third series of mice, serving as positive control, consists of groups treated with anti-IL10 antibodies given soon after weaning, and thereafter at varying dosing schedules.

Disease development is monitored in terms of eventual mortality, kidney histology, serum autoantibody levels, and proteinuria.

Example 28

This example describes a procedure to evaluate efficacy of CCR4 antagonists for treatment of malignancy.

SCID mice can be transplanted with primary human tumor cells. Normal mouse strains can be transplanted with a variety of well-characterized mouse tumor lines, including a mouse thymoma EL4 which has been transfected with OVA to allow easy evaluation of tumor specific antigen responses following vaccination with OVA. Three series of mouse groups from any of these tumor models are tested for CCR4 antagonist efficacy as follows: One series of mice additionally receives phosphate buffered saline (PBS) and Tween 0.5% i.p. soon after tumor transplant, and thereafter at varying dosing schedules. A second series consists of groups of mice receiving different doses of the CCR4 antagonist(s) given either intra-peritoneally, intra-venously, sub-cutaneously, intra-muscularly, orally, or via any other mode of administration soon after tumor transplant, and thereafter at varying dosing schedules. A third series of mice, serving as positive control, consists of groups treated with either anti-IL4 antibodies, anti-IFNg antibodies, IL4, or TNF, given i.p. soon after tumor transplant, and thereafter at varying dosing schedules.

Efficacy is monitored via tumor growth versus regression. In the case of the OVA-transfected EL4 thymoma model, cytolytic OVA-specific responses can be measured by stimulating draining lymph node cells with OVA in vitro, and measuring antigen-specific cytotoxicity at 72 hours.

Example 29

This example describes procedures to evaluate the efficacy of CCR4 antagonists in psoriasis.

A rodent model of psoriasis can be obtained by intravenously transferring a population of purified T cells (designated CD45Rbhi T cells) obtained from the spleens of BALB/c mice into immunodeficient recipient CB.17 scid/scid mice. Mice develop signs of redness, swelling, and skin lesions resembling those of human psoriasis in their ear, feet and tail by 8 weeks after transfer. Three series of mouse groups, comprising 10-15 CB.17 scid/scid mice per group, are injected with purified CD45Rbhi T cells. One series of mice additionally receives phosphate buffered saline (PBS) and Tween 0.5% i.p. at the initial cell transfer, and at different dosing schedules thereafter. A second series consists of groups of mice receiving different doses of the CCR4 antagonist(s) given either intra-peritoneally, intra-venously, sub-cutaneously, intramuscularly, orally, or via any other mode of administration at the initial cell transfer, and at different dosing schedules thereafter. A third series of mice, serving as positive control, consists of groups treated with antibodies to either IL-12, IL-4, IFNg, or TNF, or with cytokine IL-10 at the initial cell transfer, and at different dosing schedules thereafter. Animals are monitored for development of psoriatic-like lesions for 3 months after cell transfer.

Example 30

This example describes a procedure to evaluate the efficacy of CCR4 antagonists in Inflammatory Bowel Disease (IBD).

Several mouse models of IBD (including Crohn's Disease and Ulcerative Colitis) have been developed. Some of these are spontaneous models occurring in genetically engineered transgenic mice that have been depleted of certain cytokine genes (e.g. IL-10, or IL-2) by homologous recombination. Another mouse model of Inflammatory Bowel Disease is obtained by transferring highly purified populations of CD4+ T lymphocytes bearing a particular surface marker phenotype (namely CD45 RB hi) into SCID mice. Three series of mouse groups from any one of these models can be used to evaluate CCR4 antagonist efficacy as follows. One group of mice additionally receives phosphate buffered saline (PBS) and Tween 0.5% i.p. soon after weaning in the case of the spontaneous models in transgenic mice, or at time of cell transfer into SCID mice and varying dosings thereafter for the cell transfer model. A second series consists of groups of mice receiving different doses of the CCR4 antagonist(s) given either intra-peritoneally, intra-venously, sub-cutaneously, intramuscularly, orally, or via any other mode of administration soon after weaning in the case of the spontaneous models in transgenic mice, or at time of cell transfer into SCID mice and varying dosings thereafter for the cell transfer model. A third series of mice, serving as positive control, consists of groups treated with antibodies to either IFNg, or TNF, or with cytokine IL-10 soon after weaning in the case of the spontaneous models in transgenic mice, or at time of cell transfer into SCID mice and varying dosings thereafter for the cell transfer model.

Mice are evaluated for 6-8 weeks for disease development, monitored initially via weight loss and/or prolapsed rectum, and eventually by histological evaluation of the animals colon and intestinal tract.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating a disease or condition selected from asthma, atopic dermatitis, atherosclerosis, multiple sclerosis, rheumatoid arthritis and HIV infection in a subject, said method comprising administering to a subject in need of such treatment an effective amount of a compound of formula (I):

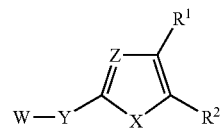

or a pharmaceutically acceptable salt thereof, wherein
W is naphthyl;
X is S;
Y is NH;
Z is N;
$R^1$ and $R^2$ are independently selected from H, halogen, CN, $CO_2R'$, CONR'R'' and $(C_1-C_8)$alkyl, wherein R' and R'' are independently selected from H, $(C_1-C_8)$ alkyl and aryl, and when R' and R'' are attached to nitrogen atom, they may be combined with the nitrogen atom to form a 5-, 6-, or 7-membered ring.

2. A method in accordance with claim 1, wherein said compound is

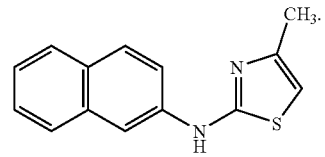

3. A method in accordance with claim 1, wherein said compound is

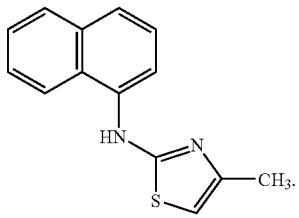

4. A method in accordance with claim 1, wherein said compound is selected from the group consisting of:

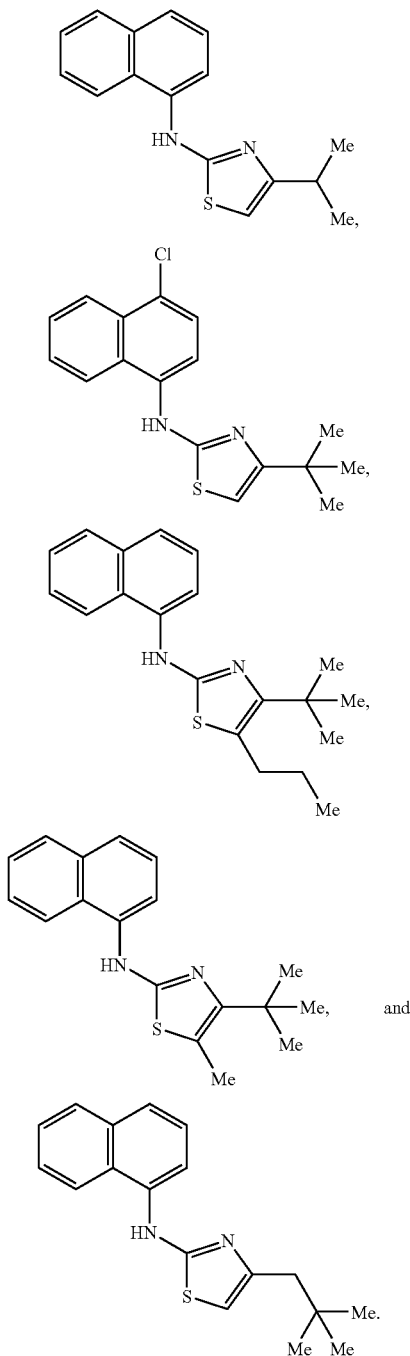

and

5. A method in accordance with claim 1, wherein said compound is

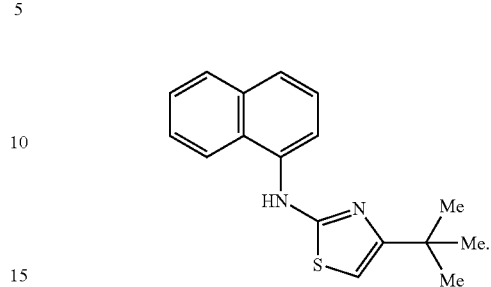

6. A method in accordance with claim 1, wherein said W is naphthyl.

7. A method in accordance with claim 1, wherein said condition or disease is atopic dermatitis.

8. A method in accordance with claim 1, wherein said condition or disease is asthma.

9. A method in accordance with claim 1, wherein said condition or disease is rheumatoid arthritis.

10. A method in accordance with claim 1, wherein said condition or disease is multiple sclerosis.

11. A method in accordance with claim 1, wherein said condition or disease is atherosclerosis.

12. A method in accordance with claim 1, wherein said disease or condition is atopic dermatitis and said compound is used alone or in combination with at least one therapeutic agent selected from a lubricant and corticosteroid.

13. A method in accordance with claim 1, wherein said condition or disease is asthma and said compound is used alone or in combination with at least one therapeutic agent selected from a β2-agonist and a corticosteroid.

14. A method in accordance with claim 1, wherein said compound interferes with the interaction between CCR4 and a ligand.

15. A method in accordance with claim 1, wherein said administration is oral or intravenous.

16. A method in accordance with claim 1, wherein said subject is selected from the group consisting of human, rat, dog, cow, horse, and mouse.

17. A method in accordance with claim 1, wherein said subject is human.

18. A method in accordance with claim 1, wherein said disease or condition is HIV infection.

* * * * *